United States Patent
Nikiforov

(10) Patent No.: US 12,091,374 B2
(45) Date of Patent: Sep. 17, 2024

(54) MONO-SUBSTITUTED CYCLOPENTADIENES AND METAL CYCLOPENTADIENYL COMPLEXES AND SYNTHESIS METHODS THEREOF

(71) Applicant: L'Air Liquide, Société Anonyme pour l'Etude et l'Exploitation des Procédés Georges Claude, Paris (FR)

(72) Inventor: Grigory Nikiforov, Bridgewater, NJ (US)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 0 days.

(21) Appl. No.: 17/578,512

(22) Filed: Jan. 19, 2022

(65) Prior Publication Data
US 2022/0135501 A1    May 5, 2022

Related U.S. Application Data

(62) Division of application No. 16/992,721, filed on Aug. 13, 2020, now Pat. No. 11,274,069.

(51) Int. Cl.
| | | |
|---|---|---|
| C07C 17/093 | (2006.01) | |
| B01J 31/02 | (2006.01) | |
| C07C 17/38 | (2006.01) | |
| C07C 22/02 | (2006.01) | |

(52) U.S. Cl.
CPC ......... *C07C 17/093* (2013.01); *B01J 31/0268* (2013.01); *C07C 17/38* (2013.01); *C07C 22/02* (2013.01)

(58) Field of Classification Search
CPC ....... C07C 17/093; C07C 17/38; C07C 22/02; C07C 2/86; C07C 13/15; C07C 17/263
See application file for complete search history.

(56) References Cited

U.S. PATENT DOCUMENTS

| | | | |
|---|---|---|---|
| 2,879,228 | A | 3/1959 | Hoeston |
| 2,953,607 | A | 9/1960 | Hafner |
| 3,152,157 | A | 10/1964 | Shapiro et al. |
| 4,915,988 | A | 4/1990 | Erbil |
| 4,927,670 | A | 5/1990 | Erbil |

(Continued)

FOREIGN PATENT DOCUMENTS

| | | |
|---|---|---|
| CN | 101293212 | 10/2008 |
| EP | 0 508 631 | 10/1992 |

(Continued)

OTHER PUBLICATIONS

Abel, E.W. et al., Some ττ-cyclopentadienyl-molybdenum and -tungsten carbonyls, J. Chem. Soc. (1960), 1321-1324.

Beachley, O.T. et al., Chemistry of In($C_5H_5$)$_3$ and some heteroleptic organoindium(III) derivatives, crystal and molecular structures of In($C_5H_5$)$_3$, ($C_5H_5$)$_3$In·PPh$_3$, and (Me$_3$CCH$_2$)$_2$In($C_5H_5$), Organometallics 2002, 21, 4632-4640.

Beachley, O.T. et al., (Pentamethylcyclopentadienl)indium(I) and -indium(III) compounds. Syntheses, reactivities, and x-ray diffraction studies of In($C_5Me_5$), Organometallics 1989, 8, 346-356.

Bock, R. et al., Röntgen-Emissionsspektralanalyse fester Stoffe, Angew. Chem. (1957), 69, 639-640.

Burkey, D.J. et al., Encapsulate4d alkaline-earth Metallocenes. 2. Triisopropylcyclopentadienyl systems, [($C_3H_7$)$_3C_5H_2$]$_2$Ae(THF)$_n$ (Ae= Ca, Sr, Ba; n=0-2), and the crystal structure of [($C_3H_7$)$_3C_5H_2$]$_2$Ba(THF)$_2$, Organometallics 1993, 12, 1331-1337.

Crane, G. et al., The preparation of cyclopentenes and cyclopentanes, J. Am. Chem. Soc. 1945, 67, 8, 1237-1239.

Holbova, E. et al., Die Reaktion nach Diels-Alder zwischen Alkylcyclopentadienen und Dienophilen vom Acryl—Typ. II. Reaktionen mit Methylvinylketon, Chem. Zvesti 23(8), 611-615 (1969) with English abstract.

(Continued)

*Primary Examiner* — Jafar F Parsa
(74) *Attorney, Agent, or Firm* — Yan Jiang

(57) ABSTRACT

A metal cyclopentadienyl complex has the formula:

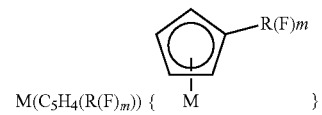

wherein m≥0; M is a Group I, II or III main group metal, alkali or transition metal; $C_5H_4$ represents a Cp ring where two hydrogens are substituted by M and R(F)$_m$; R(F)$_m$ is connected to any one of the carbon atoms of the Cp and selected from a hydrocarbyl, fluorohydrocarbyl, silyl group [SiR'$_3$], or amino group [—NR$^1$R$^2$]. The metal cyclopentadienyl complexes include Li($C_5H_4$-2-$C_5H_{11}$) (CAS No: 2413046-23-6), K($C_5H_4$-2-$C_5H_{11}$), Na($C_5H_4$-2-$C_5H_{11}$), K($C_5H_4$-1-F—$C_4H_{10}$), K($C_5H_4$-1,1,1-3F—$C_4H_6$), Li($C_5H_4$-2-$C_4H_9$), or In($C_5H_4$-2-$C_5H_{11}$) (CAS No.: 2364634-67-1).

A mono-substituted cyclopentadiene has the formula:

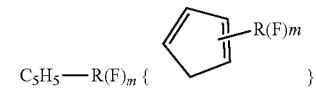

wherein m≥0; $C_5H_5$ represents the Cp ring where one hydrogen is substituted R(F)$_m$; R(F)$_m$ is connected to any one of the carbon atoms of the Cp and selected from a hydrocarbyl, fluorohydrocarbyl, silyl group [SiR'$_3$], or amino group [—NR$^1$R$^2$]. The mono-substituted cyclopentadienes include $C_5H_5$-1-F—$C_4H_{10}$, $C_5H_5$-2-$C_5H_{11}$, $C_5H_5$-2-$C_4H_9$, or $C_5H_5$-1,1,1-3F—$C_4H_6$.

6 Claims, 3 Drawing Sheets

(56) References Cited

U.S. PATENT DOCUMENTS

| | | | |
|---|---|---|---|
| 5,336,795 | A | 8/1994 | Lisowsky |
| 5,545,774 | A | 8/1996 | Rao |
| 5,574,192 | A | 11/1996 | Vanderpuy et al. |
| 5,852,223 | A | 12/1998 | Kohno et al. |
| 6,232,516 | B1 | 5/2001 | Van Beek et al. |
| 6,815,568 | B2 | 11/2004 | Horiba et al. |
| 8,785,574 | B2 | 7/2014 | Bando et al. |
| 8,975,427 | B2 | 3/2015 | Harlan et al. |
| 2004/0030204 | A1 | 2/2004 | Wilmet et al. |
| 2006/0275545 | A1 | 12/2006 | Yoshinaka et al. |
| 2009/0302434 | A1 | 12/2009 | Pallem et al. |
| 2012/0323054 | A1 | 12/2012 | Knapp |
| 2015/0126786 | A1 | 5/2015 | Sharratt et al. |
| 2020/0181775 | A1 | 6/2020 | Mizutani et al. |
| 2022/0243319 | A1* | 8/2022 | Ono .................. C23C 16/45553 |

FOREIGN PATENT DOCUMENTS

| | | |
|---|---|---|
| GB | 2 295 101 | 5/1996 |
| JP | H06 81636 | 3/1994 |
| JP | 2001 097896 | 4/2001 |
| JP | H06 321977 | 4/2001 |
| JP | 2002 338590 | 11/2002 |
| JP | 2012 176915 | 9/2012 |
| JP | 2015 110581 | 6/2015 |
| KR | 10 03 17113 | 1/2002 |
| RU | 2478576 | 4/2013 |
| RU | 2547489 | 4/2015 |
| SU | 520341 | 7/1976 |
| WO | WO 97 42151 | 11/1997 |
| WO | WO 02 27063 | 4/2002 |
| WO | WO 2018 225668 | 12/2018 |

OTHER PUBLICATIONS

Licht, A.I. et al., 2020P00195—Licht et al., CH-Activierungsreaktionen an substituierten Zirconocenkomplexen un deren Verwendung inder katalytischen Ethylenpolymerisation, J. Organomet Chem 684 (2003) 91-104, with English abstract.

Mironov, V.A. et al., Cyclic unsaturated compounds, Izvestiya Akademii Nauk SSSR, Seriya Khimicheskaya, No. 2, Feb. 1973, 376-383.

Mironov, V.A. et al., Cyclilc unsaturated compounds. 70. Metalation of cyclopentadiene by alcoholates and hydroxides of alkali metals, Izvestiya Vysshikh Uchebnykh Zavedenii, Khimiya i Khimicheskaya Tekhnologiya (1983), 26(6), 759-761.

Möhring et al., Homogenous Group 4 metallocene Ziegler-Natta Catalysts: the influence of cyclopentadienyl-ring substituents, J. Organomet. Chem., 1994, vol. 479, 1-29.

Peppe, C. et al., A simple synthesis of cyclopentadienylindium(I), J. Chem. Soc., Dalton Trans., 1981, 2592.

Poland, J.S. et al., Coordination compounds of indium. XIII. Tricyclopentadienylindium(III) and some related compounds, J Organomet. Chem. (1972), 42(2), 307-314.

Staring, E.G. et al., Organometallic vapor phase epitaxy of InP layers using the new precursors methylcyclopentadienylindium, J Am. Chem. Soc. (1989), 111(19), 7648-7650.

Tirouflet, J. et al., Complexes du titane presentant une chiralite centree sur l'atome metallique, Tetrahedron Letters (1973), (3), 257-260.

U.S. Chemical Safety and Hazard Investigation Board, Investigation Report: T2 Laboratories, Inc,. Runaway Reaction, Jacksonville, Florida, Dec. 19, 2007, Report No. 2008-3-I-FL, Sep. 2009, 1-69.

* cited by examiner

MONO-SUBSTITUTED CYCLOPENTADIENES AND METAL CYCLOPENTADIENYL COMPLEXES AND SYNTHESIS METHODS THEREOF

CROSS REFERENCE TO RELATED APPLICATIONS

This is a divisional of U.S. patent application Ser. No. 16/992,721, filed Aug. 13, 2020, the entire contents of which are incorporated herein by reference.

TECHNICAL FIELD

The present invention relates to mono-substituted cyclopentadienes and metal cyclopentadienyl complexes used as precursors in film forming compositions and methods for synthesizing them. The metal cyclopentadienyl complexes are synthesized from the mono-substituted cyclopentadienes and include main group (Group I, Group II and Group III metal) and transition metal cyclopentadienyl complexes.

BACKGROUND

Cyclopentadienyl complexes of main Groups and transition metals are widely employed as precursors for deposition of metal containing films by various deposition methods such as chemical vapor deposition (CVD) and atomic layer deposition (ALD) including metal organic CVD (MOCVD), plasma enhanced CVD (PECVD), plasma enhanced ALD (PEALD), etc. To become an optimal precursor for a given process, a transition metal complex has to fulfill to a set of requirements such as thermal stability, volatility, low melting point, optimally being liquid at room temperature, as well as possibility to form a film of certain composition and at the certain temperature range.

Chemical and physical properties of the metal complexes can be varied over a wide range by the specific choice of the substituents on the cyclopentadiene ring. A review (J. Organomet. Chem., 1994, Volume 479, 1-29) on the influence of the substituents on cyclopentadiene as a ligand in metal complexes states that however no predictions can be made concerning the effect to be expected of specific substituents.

Examples in regarding the deposition processes include indium complexes In(R-Cp) (R=$C_0$-$C_5$ aliphatic chain), where complexes InCp and In(Me-Cp) are solids, complexes with R=$C_2$-$C_4$ are light sensitive liquids and complexes with R=$C_5$ stable on light and volatile liquid. See Ang. Chem. (1957), 69, 639-640; J Organomet. Chem. (1972), 42(2), 307-314; J Am. Chem. Soc. (1989), 111(19), 7648-7650; WO WO18225668; US patent application No. 16,941,088 filed on Jul. 28, 2020.

Yttrium (Y) cyclopentadienyl complexes have also been used as deposition precursors. Complexes Y(RCp)$_3$ (R=Me, Et, Pr) are solids at room temperature, but Y($^n$BuCp)$_3$, Y($^i$BuCp)$_3$ are liquid species at room temperature. Ytterbium (Yb) compounds {(R$^1$—$C_5H_4$)(R$^2$—$C_5H_4$)(R$^3$—$C_5H_4$)Yb} (R$^1$, R$^2$=CF$_3$(CH$_2$)$_3$; R$^3$=CF$_3$(CH$_2$)$_2$) with the heavier and bulkier mono-substituted Cp ligands than PrCp have a good volatility at room temperature, while ytterbium complexes with EtCp and MeCp ligands are not volatile below 100° C. See WO 0227063; JP 2002338590; U.S. Pat. No. 4,927,670; RU 2547489; US 20090302434.

Alkyl cyclopentadienes are normally synthesized from CpNa and bromoalkane or CpMgCl and bromo- or iodoalkane. U.S. Pat. No. 897,542 to Harlan et al. discloses that the yield and subsequent purity of the product $C_5H_5$—R is highly dependent upon reaction conditions and substituent on alkyl chain, and may result in undesirable levels of impurities and low yields of the desired product. However, commercially available CpMgCl, CpNa are expensive. Their syntheses involve operating with sodium metal at high temperatures, which have safety issues. See J. Am. Chem. Soc. 1945, 67, 8, 1237-1239; U.S. Pat. No. 2,953,607; J. Organomet Chem 684 (2003) 91-104; U.S. Pat. No. 8,975,427.

Few reports are presenting alternative syntheses of mono-substituted cyclopentadienes $C_5H_5$—R. The approaches include reaction of freshly cracked cyclopentadiene with NaNH$_2$ in liquid NH$_3$, followed by MeEtCHBr to yield a mixture of 1- and 2-secbutylcyclopentadienes in a 6:4 ratio (Seriya Khimicheskaya (1973), (2), 376-383). Alternatively, freshly cracked cyclopentadiene reacts with bromoalkane in the presence of KOH, CaO, CaH$_2$ (or ROM (R=Et, $^i$Pr, M=Na, K) or CaC$_2$ in liquid ammonia, tetrahydrofurane (THF), dimethylformamide solvents without any catalyst (Mironov et al., Khimiya i Khimicheskaya Tekhnologiya (1983), 26(6), 759-761). Mironov et al. teach that the best performance of the reaction is in the presence of CaC$_2$ and CaH$_2$ with liquid ammonia solvent without any catalyst (Mironov et al., Seriya Khimicheskaya (1973), (2), 376-383; Mironov et al., to SU 520341 T).

In the other side, WO9742151 to Gruter et al. discloses a reaction of CpH, Br-Alkane, KOH and Catalyst Aliquat-336 to synthesize di- and tri-substituted $C_5H_4R_2$ and $C_5H_3R_3$ (R is an alkyl), not mono-substituted cyclopentadienes. The mono-substituted product is not possible to isolate from the reaction mixture if the reaction is performed according to the recipe, where solvent is water.

Known and widely employed metal cyclopentadienyl precursors are prepared only by a certain reaction involving a certain metal salt, $C_5H_5$—R or alkali metal cyclopentadienyl, as demonstrated for synthesis of indium complex supported with $C_5H_5$-2-$C_5H_{11}$. The $C_5H_5$-2-$C_5H_{11}$ ligand was mentioned by Abel et al. (J. Chem. Soc. (1960), 1321-1324). But the ligand was not isolated in pure form and the article presents only coordinated —$C_5H_4$-2-$C_5H_{11}$ in molybdenum (Mo) complex RC$_5H_4$Mo(CO)$_3$I (R=CHMePr"). Compound $C_5H_5$-2-$C_4H_9$ was mentioned in Mironov et al. (Seriya Khimicheskaya (1973), (2), 376-383) and Holbova et al. (Chemicke Zvesti (1969), 23(8), 611-615). However, the compound $C_5H_5$-2-$C_4H_9$ was prepared by a different, much complex route involving liquid ammonia and chromatographic separation.

RU 2478576 discloses preparation of compound $C_5H_5$-1,1,1-3F—$C_4H_6$ from CpNa and 1-Br-4,4,4-F-butane without any characterizations. RU 2478576 also discloses K(Cp-BuF$_3$) without any characterizations for preparation of a highly volatile Ytterbium complex Yb(3FBuCp)$_2$(3F-PrCp). U.S. Pat. No. 8,785,574 discloses compound $C_5H_5$-1,1,1-3F-Bu without any syntheses and characterizations.

Lithium complex was disclosed by Tirouflet et al. (Tetrahedron Letters (1973), (3), 257-260) without any characterizations and analytical data. The complex obtained by reduction of Me-Et-Fulvene with LiAlH$_4$ but no synthesis procedures provided.

WO 0227063, JP 2002338590, and US2006275545 teach that Y complexes supported by the mono-substituted cyclopentadiene ligands are prepared from anhydrous yttrium trichloride and potassium salt of the corresponding ligand. Yb complexes supported by the fluoroalkyl ligands, such as {(R$^1$—$C_5H_4$)(R$^2$—$C_5H_4$)(R$^3$—$C_5H_4$)Yb} (R$^1$, R$^2$=CF$_3$(CH$_2$)$_3$, R$^3$=CF$_3$(CH$_2$)$_2$), which are volatile liquids at room temperature, are prepared from the corresponding potassium compounds K(R″—C$_5$H$_4$) and YbCl$_3$. See RU 2547489.

Burkey et al. (Organometallics 1993, 12, 1331-1337) disclose strontium (Sr) and barium (Ba) complexes M(Cp-R)$_2$ (M=Sr, Ba) with the substituted cyclopentadiene ligands can be prepared only from potassium compounds, e.g. from K((C$_3$H$_7$)$_3$C$_5$H$_2$) and SrI$_2$ or BaI$_2$. The reaction of K((C$_3$H$_7$)$_3$C$_5$H$_2$) and SrCl$_2$ does not proceeds and SrCl$_2$ and K((C$_3$H$_7$)$_3$ C$_5$H$_2$) are recovered. The reaction of Li((C$_3$H$_7$)$_3$C$_5$H$_2$) and SrCl$_2$ does not proceed and SrCl$_2$ and K((C$_3$H$_7$)$_3$C$_5$H$_2$) are recovered. Alternatively, U.S. Pat. No. 4,915,988 discloses Sr and Ba complexes with substituted cyclopentadienyl ligands can be prepared only from the pure cyclopentadienyl ligands and Sr or Ba metals at high temperature (500° C.-600° C.).

Indium complexes In(R-Cp) (R=C$_0$-C$_4$ aliphatic chain) are prepared by the unique reaction starting from InCl and the lithium salt of the ligand (J. Chem. Soc., Dalton Trans., 1981, 2592). The original reaction from InCl$_3$ and NaCp performed in gram scale involves thermal decomposition step of InCp$_3$, afford InCp in a low yield and gives a poorly separable complex mixture of compounds for the cases with the substituted cyclopentadienyl ligand. See Organometallics 1989, 8, 346-356; Organometallics 2002, 21, 4632-4640.

These imply that in order to prepare a suitable proper precursor, a wide range of substituents R in metal cyclopentadienyls (or alkali metal cyclopentadienyls) M(Cp-R) complexes of a given metal needs to be screened and a selection of an ideal combination of starting materials that provides a high stability, volatility and low melting point, ideally making M(Cp-R) as liquid at room temperature, is demanded. Hence there is a need for a simple, robust and economical method to prepare substituted cyclopentadienes C$_5$H$_5$-Rs and/or corresponding metal complexes, which may serve as a starting compound for forming a targeted film forming composition.

SUMMARY

Disclosed are methods of synthesizing a metal cyclopentadienyl complex, the method comprising:
mixing a metal hydroxide, a halide, a cyclopentadiene monomer, an alkaline earth oxide, and a catalyst in a solvent;
allowing a selective catalytic carbon-carbon coupling reaction to form a mono-substituted cyclopentadiene;
contacting the mono-substituted cyclopentadiene with a metal compound; and
converting the mono-substituted cyclopentadiene to the metal cyclopentadienyl complex. The disclosed methods may include one or more of the following aspects:
further comprising maintaining a temperature within a range of from −15° C. to 70° C. under atmospheric pressure;
further comprising maintaining a temperature below 40° C. under atmospheric pressure;
further comprising maintaining a temperature within a range of from 15° C. to 35° C. under atmospheric pressure;
further comprising maintaining a temperature within a range of from 20° C. to 30° C. under atmospheric pressure;
further comprising maintaining a temperature below 5° C. under atmospheric pressure;
further comprising maintaining a temperature within a range of from −5° C. to 0° C. under atmospheric pressure;
further comprising maintaining a pressure around atmospheric pressure;
further comprising maintaining an air atmosphere;
further comprising maintaining an inert gas atmosphere, such as N$_2$, a noble gas (i.e., He, Ne, Ar, Kr, Xe);
further comprising maintaining a N$_2$ atmosphere;
further comprising maintaining an Ar atmosphere;
further comprising optionally purifying the mono-substituted cyclopentadiene;
further comprising purifying the mono-substituted cyclopentadiene;
further comprising not purifying the mono-substituted cyclopentadiene;
approximately 20-400% excess amount of the cyclopentadiene monomer being used relative to the amount of the halide;
approximately 40-80% excess amount of the cyclopentadiene monomer being used relative to the amount of the halide;
the optimized selectivity of the process being achieved when approximately 20-400% excess of CpH monomer is used relative to R(Hal) or R(F)(Hal);
the optimized selectivity of the process being achieved when approximately 40-80% excess of CpH monomer is used relative to R(Hal) or R(F)(Hal);
the metal hydroxide being MOH, wherein M being Group I alkali metal;
MOH being NaOH;
MOH being KOH;
the halide R(Hal) or R(F)(Hal) being an silyl-, amino-, alkyl- or hydrocarbonyl halide or fluoroalkyl halide has the formula R(Hal) or R(F)(Hal), wherein Hal is selected from Cl, Br, I; R is selected from
a C$_1$-C$_8$ linear or branched, saturated or unsaturated hydrocarbyl group;
a C$_1$-C$_8$ linear or branched, saturated or unsaturated fluorohydrocarbyl group containing at least one fluorine;
a silyl group [SiR'$_3$] with R' being selected from H, a C$_1$-C$_4$ saturated or unsaturated hydrocarbyl group;
a silyl group [SiR'$_3$] with each R' being selected from H, F, a C$_1$-C$_4$ saturated or unsaturated fluorohydrocarbyl group containing at least one fluorine atom; and
an amino group [—NR$^1$R$^2$] with each R$^1$ and R$^2$ being independently selected from H or a C$_1$-C$_6$ linear or branched, saturated or unsaturated hydrocarbyl group.
the alkaline earth oxide being MO, wherein M is Group II alkaline earth metal;
MO being CaCO$_2$;
the catalyst being a tertiary phosphonium salt;
the catalyst being tetrabutylphosphonium chloride, Bu$_4$PCl (CAS No: 2304-30-5);
the catalyst being PPent$_4$Cl (Pent=C$_5$H$_{11}$) or PPh$_4$Cl (Ph=C$_6$H$_5$);
the metal compound being an alkyl metal compound selected from MeLi or BuLi;
the metal compound being a metal hydride MH, wherein M is a Group I, Group II or Group III main group metal or a transition metal selected from K, Na, Sr, Ba, Ga, In, Y or Yb;
the metal compound being a metal hydride MH, wherein M is a Group I, Group II or Group III main group metal;
the metal compound being a metal hydride MH, wherein M is a transition metal selected from K, Na, Sr, Ba, Ga, In, Y or Yb;

the metal hydride being an alkali metal hydride;
the alkali metal hydride being NaH;
the alkali metal hydride being KH;
the solvent being a furan solvent;
the solvent being THF;
the solvent being Me-THF;
the mono-substituted cyclopentadiene being 1-fluorobutyl-cyclopentadiene ($C_5H_5$-1-F—$C_4H_{10}$, $C_5H_5$-1-F-Bu), 2-pentyl-cyclopentadiene ($C_5H_5$-2-$C_5H_{11}$, $C_5H_5$-2-Pent), 2-butyl-cyclopentadiene ($C_5H_5$-2-$C_4H_9$, $C_5H_5$-2-Bu), or 1,1,1-trifluoropropyl-cyclopentadiene ($C_5H_5$-1,1,1-3F—$C_4H_9$, $C_5H_5$-3F-Bu);
the mono-substituted cyclopentadiene being 1-fluorobutyl-cyclopentadiene ($C_5H_5$-1-F—$C_4H_{10}$, $C_5H_5$-1-F-Bu);
the mono-substituted cyclopentadiene being 2-pentyl-cyclopentadiene ($C_5H_5$-2-$C_5H_{11}$);
the mono-substituted cyclopentadiene being 2-butyl-cyclopentadiene ($C_5H_5$-2-$C_4H_9$, $C_5H_5$-2-Bu);
the mono-substituted cyclopentadiene being 1,1,1-trifluoropropyl-cyclopentadiene ($C_5H_5$-1,1,1-3F—$C_4H_6$, $C_5H_5$-3F-Bu);
the metal cyclopentadienyl precursor being Li($C_5H_4$-2-$C_5H_{11}$) (Li(Cp-2-Pent), CAS No: 2413046-23-6), K($C_5H_4$-2-$C_5H_{11}$) (K(Cp-2-Pent)), Na($C_5H_4$-2-$C_5H_{11}$) (Na(Cp-2-Pent)), K($C_5H_4$-1-F—$C_4H_{10}$) (K(Cp-1-F-Bu)), K($C_5H_4$-1,1,1-3F—$C_4H_6$) (K(Cp-1,1,1-3F-Bu)), Li($C_5H_4$-2-$C_4H_9$) (Li(Cp-2-Bu)), or In($C_5H_4$-2-$C_5H_{11}$) (In(Cp-2-Pent), CAS No.: 2364634-67-1);
the metal cyclopentadienyl precursor being Li($C_5H_4$-2-$C_5H_{11}$) (Li(Cp-2-Pent), CAS No: 2413046-23-6);
the metal cyclopentadienyl precursor being K($C_5H_4$-2-$C_5H_{11}$) (K(Cp-2-Pent));
the metal cyclopentadienyl precursor being Na($C_5H_4$-2-$C_5H_{11}$) (Na(Cp-2-Pent));
the metal cyclopentadienyl precursor being K($C_5H_4$-1-F—$C_4H_{10}$) (K(Cp-1-F-Bu));
the metal cyclopentadienyl precursor being K($C_5H_4$-1,1,1-3F—$C_4H_9$) (K(Cp-1,1,1-3F-Bu));
the metal cyclopentadienyl precursor being Li($C_5H_4$-2-$C_4H_9$) (Li(Cp-2-Bu));
the metal cyclopentadienyl precursor being In($C_5H_4$-2-$C_5H_{11}$) (In(Cp-2-Pent), CAS No.: 2364634-67-1);
Disclosed is a metal cyclopentadienyl complex having the following formula:

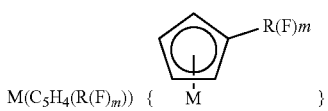

wherein m≥0; M is a main group, alkali or transition metal; $C_5H_4$ represents a cyclopentadienyl (Cp) ring where two hydrogens are substituted by M and $R(F)_m$, respectively; $R(F)_m$ is connected to any one of the carbon atoms of the Cp and selected from
i) a $C_1$-$C_8$ linear or branched, saturated or unsaturated hydrocarbyl group;
ii) a $C_1$-$C_8$ linear or branched, saturated or unsaturated fluorohydrocarbyl group containing at least one fluorine;
iii) a silyl group [$SiR'_3$] with each R' being selected from H, a $C_1$-$C_4$ saturated or unsaturated hydrocarbyl group;
iv) a silyl group [$SiR'_3$] with R' being independently selected from H, F, a $C_1$-$C_4$ saturated or unsaturated fluorohydrocarbyl group containing at least one fluorine atom; and
v) an amino group [—$NR^1R^2$] with $R^1$ and $R^2$ each being selected from H or a $C_1$-$C_6$ linear or branched, saturated or unsaturated hydrocarbyl group.

The disclosed metal cyclopentadienyl complex may include one or more of the following aspects:
R being selected from n-Pr, i-Pr, n-Bu, i-Bu, 2-Bu, n-Pent, i-Pent, 2-Pent, n-Hex, i-Hex, 2-Hex, n-Hept, i-Hept, 2-Hept, —$CF_3$, –1,1,1-trifluoropropane (–1,1,1-$PrF_3$), –1,1,1-trifluorobutane (–1,1,1-$BuF_3$), or –1-fluorobutane (–1,1,1-BuF);
M being a Group I, Group II or Group III main group metal or a transition metal;
M being selected from K, Na, Sr, Ba, Ga, In, Y or Yb;

Disclosed is a mono-substituted cyclopentadiene having the following formula:

wherein m≥0; $C_5H_5$ represents a cyclopentadienyl (Cp) ring where one hydrogen is substituted $R(F)_m$; $R(F)_m$ is connected to any one of the carbon atoms of the Cp and selected from
a. a $C_1$-$C_8$ linear or branched, saturated or unsaturated hydrocarbyl group;
b. a $C_1$-$C_8$ linear or branched, saturated or unsaturated fluorohydrocarbyl group containing at least one fluorine atom;
c. a silyl group [$SiR'_3$] with R' being selected from H, a $C_1$-$C_4$ saturated or unsaturated hydrocarbyl group;
d. a silyl group [$SiR'_3$] with R' being selected from H, F, a $C_1$-$C_4$ saturated or unsaturated fluorohydrocarbyl group containing at least one fluorine atom; and
e. an amino group [—$NR^1R^2$] with $R^1$ and $R^2$ each being independently selected from H or a $C_1$-$C_6$ linear or branched, saturated or unsaturated hydrocarbyl group.

The disclosed mono-substituted cyclopentadiene may include one or more of the following aspects:
R is selected from n-Pr, i-Pr, n-Bu, i-Bu, 2-Bu, n-Pent, i-Pent, 2-Pent, n-Hex, i-Hex, 2-Hex, n-Hept, i-Hept, 2-Hept, —$CF_3$, –1,1,1-trifluoropropane (–1,1,1-$PrF_3$), –1,1,1-trifluorobutane (–1,1,1-$BuF_3$), or –1-fluorobutane (–1,1,1-BuF).

Notation and Nomenclature

The following detailed description and claims utilize a number of abbreviations, symbols, and terms, which are generally well known in the art.

As used herein, the indefinite article "a" or "an" means one or more.

As used herein, "about" or "around" or "approximately" in the text or in a claim means±10% of the value stated.

As used herein, "room temperature" in the text or in a claim means from approximately 18° C. to approximately 25° C.

As used herein, "atmospheric pressure" in the text or in a claim means approximately 1 atm.

The standard abbreviations of the elements from the periodic table of elements are used herein. It should be understood that elements may be referred to by these abbreviation (e.g., Si refers to silicon, N refers to nitrogen, O refers to oxygen, C refers to carbon, H refers to hydrogen, Hal refers to halogens, which are F, Cl, Br, I).

The unique CAS registry numbers (i.e., "CAS") assigned by the Chemical Abstract Service are provided to identify the specific molecules disclosed.

As used herein, the term "hydrocarbon" refers to a saturated or unsaturated function group containing exclusively carbon and hydrogen atoms.

As used herein, the term "hydrocarbyl" refers to any univalent radical, derived from a hydrocarbon, such as methyl or phenyl.

As used herein, the term "fluorohydrocarbon" refers to a saturated or unsaturated function group containing exclusively carbon, hydrogen and fluorine atoms.

As used herein, the term "fluorohydrocarbyl" refers to any univalent radical, derived from a fluorohydrocarbon.

As used herein, the term "alkyl group" refers to saturated functional groups containing exclusively carbon and hydrogen atoms. An alkyl group is one type of hydrocarbon. Further, the term "alkyl group" refers to linear, branched, or cyclic alkyl groups. Examples of linear alkyl groups include without limitation, methyl groups, ethyl groups, propyl groups, butyl groups, etc. Examples of alkyl groups include without limitation, methyl (Me), butyl (Bu), pentyl (Pent), etc. Examples of branched alkyl groups include without limitation, t-butyl (t-Bu), etc.

As used in the disclosed embodiments, the abbreviation "Me" refers to a methyl group; the abbreviation "Et" refers to an ethyl group; the abbreviation "Pr" refers to a propyl group; "Bu" refers to a butyl group; "Pent" refers to a pentyl group.

As used herein, the term "fluoroalkyl group" or "fluorinated alkyl group" refers to a saturated functional group containing carbon, hydrogen and at least one fluorine. An fluoroalkyl group is one type of fluorohydrocarbon. Further, the term "fluoroalkyl group" refers to a linear, branched, or cyclic fluoroalkyl group.

As used herein the "halides" are represented as R(Hal) and/or R(F)(Hal) in which Hal is selected from Cl, Br, I; R is selected from
a. a $C_1$-$C_8$ linear or branched, saturated or unsaturated hydrocarbyl group;
b. a $C_1$-$C_8$ linear or branched, saturated or unsaturated fluorohydrocarbyl group containing at least one fluorine;
c. a silyl group [SiR'$_3$] with R' being selected from H, a $C_1$-$C_4$ saturated or unsaturated hydrocarbyl group;
d. a silyl group [SiR'$_3$] with each R' being selected from H, F, a $C_1$-$C_4$ saturated or unsaturated fluorohydrocarbyl group containing at least one fluorine atom; and
e. an amino group [—NR$^1$R$^2$] with each R$^1$ and R$^2$ being independently selected from H or a $C_1$-$C_6$ linear or branched, saturated or unsaturated hydrocarbyl group.

The term "CpH" used herein refers to a cyclopentadiene molecule or cyclopentadiene monomer ($C_5H_6$).

The term "Cp" used herein refers to a cyclopentadienyl ring in which one or more than one hydrogens are substituted. Cp may be a $C_5H_5$ ring (one hydrogen is substituted), a $C_5H_4$ ring (two hydrogens are substituted), a $C_5H_3$ ring (three hydrogens are substituted), etc. The term "Cp" used herein also refers to a cyclopentadienyl anion or a substituted cyclopentadienyl anion, such as a cyclopentadienyl anion or a substituted cyclopentadienyl anion in a metal cyclopentadienyl complex. Here the "cyclopentadienyl" in the metal cyclopentadienyl complex refers to any cyclopentadienyls including substituted cyclopentadienyls.

The term "Cp$_2$" used herein refers to a cyclopentadiene dimer ($C_{10}H_{12}$).

The term "mono-substituted cyclopentadiene" is used herein because only one R(F)$_m$ (m≥0) group is connected to any one of the carbon atoms on the cyclopentadiene ring. The mono-substituted cyclopentadiene has a general formula $C_5H_5$—(R(F)$_m$) (m≥0, R has the same definition as the "halides" described above).

In the present context, a homogeneous catalyst is understood to mean a catalyst that is present in the same phase as the reactants.

Ranges may be expressed herein as from about one particular value, and/or to about another particular value. When such a range is expressed, it is to be understood that another embodiment is from the one particular value and/or to the other particular value, along with all combinations within said range. Any and all ranges recited herein are inclusive of their endpoints (i.e., x=1 to 4 or x ranges from 1 to 4 includes x=1, x=4, and x=any number in between), irrespective of whether the term "inclusively" is used.

Reference herein to "one embodiment" or "an embodiment" means that a particular feature, structure, or characteristic described in connection with the embodiment may be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used herein, the term "independently" when used in the context of describing R groups should be understood to denote that the subject R group is not only independently selected relative to other R groups bearing the same or different subscripts or superscripts, but is also independently selected relative to any additional species of that same R group. For example in the formula MR$^1_x$ (NR$^2$R$^3$)$_{(4-x)}$, where x is 2 or 3, the two or three R$^1$ groups may, but need not be identical to each other or to R$^2$ or to R$^3$. Further, it should be understood that unless specifically stated otherwise, values of R groups are independent of each other when used in different formulas.

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

BRIEF DESCRIPTION OF THE DRAWINGS

The foregoing and various other aspects, features, and advantages of the present invention, as well as the invention itself, may be more fully appreciated with reference to the following detailed description of the invention when considered in connection with the following drawings. The drawings are presented for the purpose of illustration only and are not intended to be limiting of the invention, in which.

DESCRIPTION OF PREFERRED EMBODIMENTS

Figure 1:
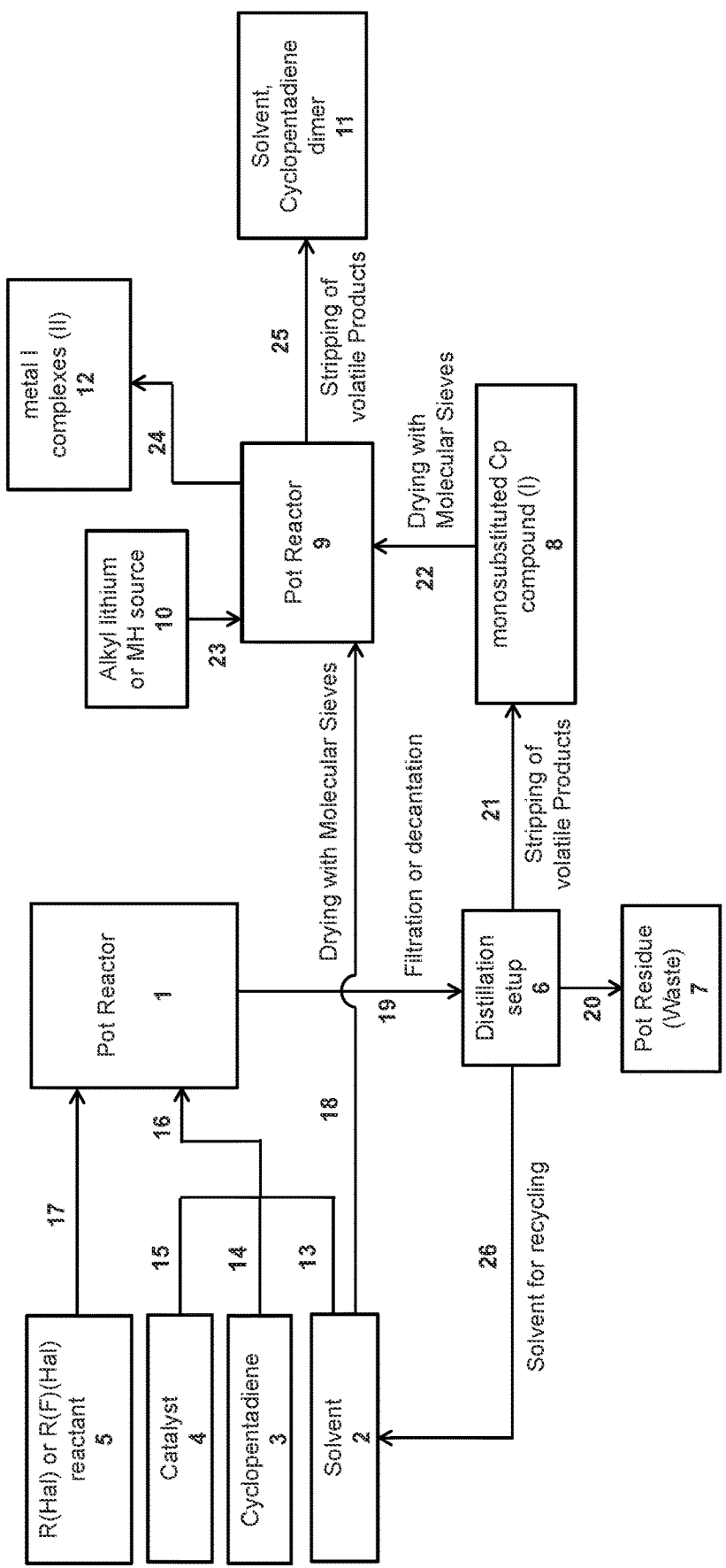
FIG. 1 is a diagram of a batch process for selective catalytic syntheses of the mono-substituted cyclopentadienes (I) and their corresponding metal Cp complexes (II)

Disclosed are mono-substituted cyclopentadienes, metal cyclopentadienyl complexes and methods for synthesizing them. The disclosed mono-substituted cyclopentadienes are synthesized by a selective catalytic carbon-carbon coupling reaction. The disclosed metal cyclopentadienyl complexes are synthesized from the disclosed mono-substituted cyclopentadienes. The disclosed metal cyclopentadienyl complexes include main group (such as Group I, Group II and Group III) metal and transition metal cyclopentadienyl complexes, and may be used as deposition precursors contained in film forming compositions for film depositions in semiconductor industry, such as ALD, CVD, SOD, etc.

The disclosed mono-substituted cyclopentadienes have the following formula:

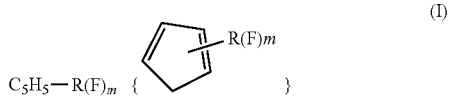

(I)

wherein m≥0; $C_5H_5$ represents a cyclopentadienyl (Cp) ring where one hydrogen is substituted by $R(F)_m$; $R(F)_m$ is connected to any one of the carbon atoms on the Cp and selected from i) a $C_1$-$C_8$ linear or branched, saturated or unsaturated hydrocarbyl group;

ii) a $C_1$-$C_8$ linear or branched, saturated or unsaturated fluorohydrocarbyl group containing at least one fluorine atom;

iii) a silyl group [$SiR'_3$] with R' being selected from H, a $C_1$-$C_4$ saturated or unsaturated hydrocarbyl group;

iv) a silyl group [$SiR'_3$] with R' being selected from H, F, a $C_1$-$C_4$ saturated or unsaturated fluorohydrocarbyl group containing at least one fluorine atom; and v) an amino group [—$NR^1R^2$] with $R^1$ and $R^2$ each being independently selected from H or a $C_1$-$C_6$ linear or branched, saturated or unsaturated hydrocarbyl group.

In the above formula (I), the hydrocarbyl group may be an alkyl group; the fluorohydrocarbyl group may be a fluoroalkyl or fluorinated alkyl group. Preferably R is selected from n-Pr, i-Pr, n-Bu, i-Bu, 2-Bu, n-Pent, i-Pent, 2-Pent, n-Hex, i-Hex, 2-Hex, n-Hept, i-Hept, 2-Hept, —$CF_3$, -1,1,1-trifluoropropane (-1,1,1-$PrF_3$), -1,1,1-trifluorobutane (-1,1,1-$BuF_3$), or -1-fluorobutane (-1,1,1-BuF). Hereinafter, $C_5H_5$—R or $C_5H_5$—$R(F)_m$ (m≥0) will represent the mono-substituted cyclopentadiene (I).

The disclosed mono-substituted cyclopentadienes (I) may be used to synthesize the metal cyclopentadienyl (Cp) complexes (II) for use as deposition precursors in film deposition. The disclosed metal Cp complexes (II) may be main Group metal or alkali metal Cp complexes and/or transition metal Cp complexes. The disclosed metal Cp complexes (II) having the following formula:

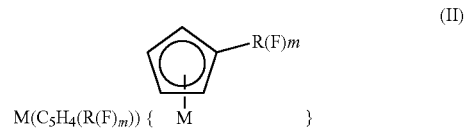

(II)

wherein m≥0; M is a main Group metal or transition metal; $C_5H_4$ represents a cyclopentadienyl (Cp) ring where two hydrogens are substituted by M and $R(F)_m$, respectively; $R(F)_m$ is connected to any one of the carbon atoms of the Cp and selected from i) a $C_1$-$C_8$ linear or branched, saturated or unsaturated hydrocarbyl group;

ii) a $C_1$-$C_8$ linear or branched, saturated or unsaturated fluorohydrocarbyl group containing at least one fluorine;

iii) a silyl group [$SiR'_3$] with each R' being selected from H, a $C_1$-$C_4$ saturated or unsaturated hydrocarbyl group;

iv) a silyl group [$SiR'_3$] with R' being independently selected from H, a fluorine atom, a $C_1$-$C_4$ saturated or unsaturated fluorohydrocarbyl group containing at least one fluorine atom; and v) an amino group [—$NR^1R^2$] with $R^1$ and $R^2$ each being selected from H or a $C_1$-$C_6$ linear or branched, saturated or unsaturated hydrocarbyl group.

In the above formula (II), the hydrocarbyl group may be an alkyl group; the fluorohydrocarbyl group may be a fluoroalkyl or fluorinated alkyl group. Preferably R is selected from n-Pr, i-Pr, n-Bu, i-Bu, 2-Bu, n-Pent, i-Pent, 2-Pent, n-Hex, i-Hex, 2-Hex, n-Hept, i-Hept, 2-Hept, —$CF_3$, -1,1,1-trifluoropropane (-1,1,1-$PrF_3$), -1,1,1-trifluorobutane (-1,1,1-$BuF_3$), or -1-fluorobutane (-1,1,1-BuF). M is coordinated to the Cp ring. Preferably, M is a Group I, Group II and Group III metal including alkali metals and transition metal including Lanthanides. Preferably, M=Li, Na, K, Ga, In, Sr, Ba, Y or Yb. Hereinafter, M($C_5H_4$—R), M(Cp-R), M($C_5H_4$—R(F)) or M(Cp-R(F)) will represent the disclosed metal Cp complexes (II).

The disclosed mono-substituted cyclopentadienes (I) and metal Cp complexes (II) have non-branched and branched alkyl or hydrocarbyl chain R or fluoroalkyl or fluorohydrocarbyl chain R(F) containing from a $C_1$ to $C_8$ chain, preferably a $C_3$ to $C_7$ chain. This chain length in the ligand may allow the metal Cp complex to tune the properties of the whole complex or precursor, namely improve stability, reduce the melting point and tune the volatility of the molecule for a suitable precursor in the film forming composition for film deposition.

Although some of the substituted cyclopentadienes with a $C_1$ or $C_2$ ligand and the corresponding alkali metal salts/complexes are known, information about $C_5H_5$—R with the R having 4 or more carbon atoms is rare or absent in the art.

Exemplary disclosed mono-substituted cyclopentadienes (I) include 1,1,1-trifluorobutyl-cyclopentadiene (1,1,1-BuF$_3$—C$_5$H$_5$, C$_5$H$_5$-1,1,1-3F-Bu),

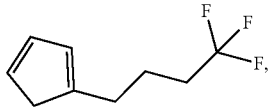 [SMILES: FC(F)(F)CCCC1=CC=CC1]

1-fluorobutyl-cyclopentadiene (1-BuF—C$_5$H$_5$, C$_5$H$_5$-1-F-Bu),

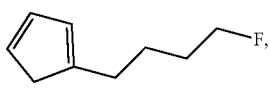

2-pentyl-cyclopentadiene (2-C$_5$H$_{11}$—C$_5$H$_5$, C$_5$H$_5$-2-Pent),

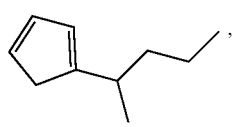

2-butyl-cyclopentadiene (2-C$_4$H$_9$—C$_5$H$_5$, C$_5$H$_5$-2-Bu)

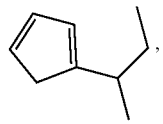

trifluoromethyl-cyclopentadiene (CF$_3$—C$_5$H$_5$, C$_5$H$_5$-3F-Me),

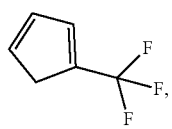

1,1,1-trifluoropropyl-cyclopentadiene (1,1,1-PrF$_3$—C$_5$H$_5$, C$_5$H$_5$-1,1,1-3F-Pr)

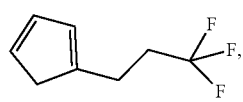 [SMILES: FC(F)(F)CCC1=CC=CC1]

n-pentyl-cyclopentadiene (n-C$_5$H$_1$—C$_5$H$_5$, C$_5$H$_5$-n-Pent)

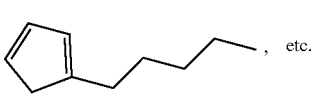, etc.

Exemplary disclosed metal Cp complexes (II) include K(Cp-n-Pr) (K(C$_5$H$_4$-n-C$_3$H$_7$))

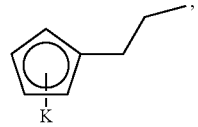

Li(Cp-2-Pent) (Li(C$_5$H$_4$-2-C$_5$H$_{11}$), CAS No: 2413046-23-6)

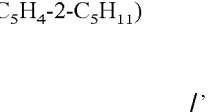

K(Cp-2-Pent) (K(C$_5$H$_4$-2-C$_5$H$_{11}$)

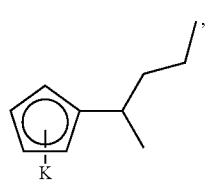

Na(Cp-2-Pent) (Na(C$_5$H$_4$-2-C$_5$H$_{11}$)

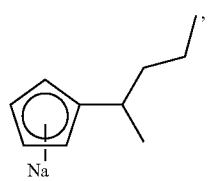

K(Cp-n-Bu) (K(C$_5$H$_4$-n-C$_4$H$_9$), CAS No.: 78347-55-4)

K(Cp-n-Pent) (K(C$_5$H$_4$-n-C$_5$H$_{11}$), CAS No.: 1010453-51-6)

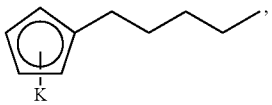

K(Cp-n-Hex) (K(C$_5$H$_4$-n-C$_5$H$_{13}$))

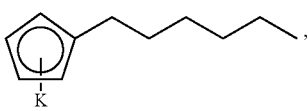

K(Cp-1-F-Bu) (K(C$_5$H$_4$-1-F—C$_4$H$_{10}$))

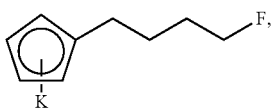

K(Cp-1,1,1-3F-Bu) (K(C$_5$H$_4$-1,1,1-3F—C$_4$H$_6$))

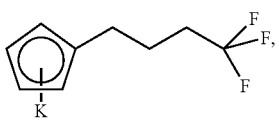

Li(Cp-2-Bu) (Li(C$_5$H$_4$-2-C$_4$H$_9$))

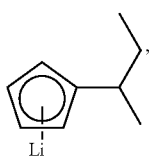

In(Cp-2-Pent) (In(C$_5$H$_4$-2-C$_5$H$_{11}$), CAS No.: 2364634-67-1)

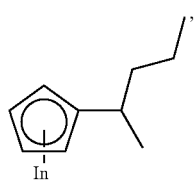

In(Cp-2-Bu) (In(C$_5$H$_4$-2-C$_4$H$_9$))

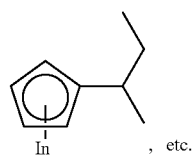

, etc.

The disclosed synthesis method for synthesizing the mono-substituted cyclopentadienes (I) is a selective catalytic carbon-carbon coupling method that provides a practical and scalable synthesis method through tuning and optimizing reaction conditions that favor a product in a high yield and minimize effects of side reactions. The selective catalytic carbon-carbon coupling method utilizes commonly available starting compounds, such as metal hydroxide (e.g., KOH or NaOH), alkyl halide R(Hal) or fluoroalkyl halide R(F)(Hal), cyclopentadiene monomer (i.e., CpH, CAS No.: 26912-33-4), alkaline earth oxide (e.g., CaO), tertiary phosphonium salt (e.g., tetrabutylphosphonium chloride, Bu$_4$PCl, CAS No: 2304-30-5). These starting compounds are stable in air. Thus, it is not necessary to dry a solvent such as THF prior to synthesis and the starting compounds and solvent can be loaded in air. Reactions are performed under mild conditions, such as the temperature ranging from −15° C. to 70° C. under 1 atm and may be performed in commonly utilized glassware or synthesis reactors. The reactions may be applied for syntheses of a wide range of substituted cyclopentadienes. Here the tertiary phosphonium salt (e.g., Bu$_4$PCl) is used as a catalyst that efficiently and selectively promotes the reaction. To our knowledge, it has not yet been possible in the art to successfully synthesize substituted cyclopentadienes using a combination of the aforementioned starting compounds including the catalyst tertiary phosphonium salt disclosed herein.

The disclosed mono-substituted cyclopentadienes (I) are produced from CpH, and silyl-, amino-, alkyl halide R(Hal) or fluorinated silyl-, amino-, alkyl halide R(F)(Hal), where halogen is selected from Cl, Br, I. The disclosed synthesis method of the mono-substituted cyclopentadienes (I) comprises the step of contacting CpH and an alkyl halide R(Hal) or a fluoroalkyl halide R(F)(Hal) in the presence of metal hydroxide (e.g., KOH or NaOH), alkaline earth oxide (e.g., CaO), and a catalyst (e.g., Bu$_4$P(Cl)) to form the mono-substituted cyclopentadiene (I). The method may further comprise distilling the mono-substituted cyclopentadiene (I) from the reaction mixture and converting it to the metal Cp complex (II).

The disclosed methods for syntheses of the metal Cp complex (II) comprise the step of contacting the mono-substituted cyclopentadiene (I) and alkyl metal compound or alkali metal hydride in a furan solvent such as THF. The metal Cp complex (II) is formed by a metalation chemical process occurred in the mixture of the mono-substituted cyclopentadiene (I) and the alkali metal hydride such as NaH or KH, or the alkyl metal compound such as alkyl-lithium compound. The method may further comprise removing all volatile species from the metal Cp complex (II).

Sodium and potassium hydrides are cheaper than alkyllithium compounds and safer to operate in the large quantities, especially when compounds are packed in sealed dissolvable bags or utilized as suspension in mineral oil. The solvent THF allows having a high volumetric efficiency, which is important for scaling up the reaction.

For example, from the example that follows, the disclosed 2-pentyl-cyclopentadiene (2-C$_5$H$_{11}$—C$_5$H$_5$, H(Cp-2-Pent)) may be produced by the selective catalytic carbon-carbon coupling reaction from freshly cracked CpH from a cyclopentadiene dimer Cp$_2$ and 2-bromo-pentane (2-Br—C$_5$H$_{11}$) in the presence of solid KOH and CaO and Bu$_4$PCl catalyst. The exemplary schematic reaction is as follows.

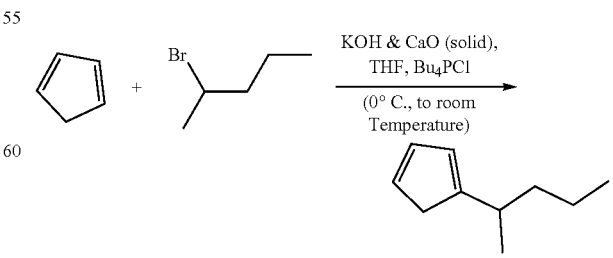

Replacing 2-bromo-pentane with n-pentyl-bromide, 2-bromo-butane, iodo-trifluoromethane, 4-bromo-1,1,1-trifluorobutane, 3-bromo-1,1,1-trifluoropropane or 4-bromo-1-fluoro-butane, the n-pentyl-cyclopentadiene (n-$C_5H_{11}$—$C_5H_5$), 2-butyl-cyclopentadiene (2-$C_4H_9$—$C_5H_5$), trifluoromethyl-cyclopentadiene ($CF_3$—$C_5H_5$), 1,1,1-trifluorobutyl-cyclopentadiene (1,1,1-$BuF_3$—$C_5H_5$), 1,1,1-trifluoropropyl-cyclopentadiene (1,1,1-$PrF_3$—$C_5H_5$), 1-fluorobutyl-cyclopentadiene (1-BuF—$C_5H_5$) may be produced.

CpH ($C_5H_6$, hereinafter a CpH monomer) can be obtained by cracking of a dicyclopentadiene dimer ($Cp_2$, $C_{10}H_{12}$, CAS No.: 77-73-6) by any suitable means disclosed in the art.

Freshly cracked CpH monomer is used for the aforementioned reaction. Due to its well-known ability to dimerize, CpH monomer is used right after cracking or stored at low temperature from −100° C. to −20° C., preferably from −70° C. to −40° C. Prior to use, CpH is always analyzed by proton NMR, GC or any other suitable analytical methods to determine the relative amount of CpH monomer $C_5H_6$ and $Cp_2$ dimer $C_{10}H_{12}$. According to the analysis, the amount of mixture containing CpH monomer and $Cp_2$ dimer is calculated for the optimal molar ratio of cyclopentadiene monomer to R(Hal) or R(F)(Hal) in the catalytic C—C coupling reaction.

Halogen in the starting compound alkyl or hydrocarbkyl halide R(Hal) is selected from Cl, Br, I, where R is selected from a $C_1$-$C_8$ linear or branched, saturated or unsaturated hydrocarbyl group; a silyl group [$SiR'_3$] with R' being selected from H, a fluorine atom a $C_1$-$C_4$ saturated or unsaturated hydrocarbyl group; or an amino group [—$NR^1R^2$] with $R^1$ and $R^2$ each being independently selected from H or a $C_1$-$C_6$ linear or branched, saturated or unsaturated hydrocarbyl group. Exemplary R(Hal)s include alkyl bromide R—Br or alkyl iodide R—I, such as, 2-Br-pentane, 2-Br-butane, or 2-Br-propane, etc.

Halogen in the starting compound fluoroalkyl halide R(F)(Hal) is selected from Cl, Br, I, where R(F) is selected from a $C_1$-$C_8$ linear or branched, saturated or unsaturated fluorohydrocarbyl group containing at least one fluorine atom; or a silyl group [$SiR'_3$] with R' being selected from H, F, a $C_1$-$C_4$ saturated or unsaturated fluorohydrocarbyl group containing at least one fluorine atom. Exemplary R(F)(Hal) include 1-Br-4,4,4-trifluorobutane, 3-Br-1,1,1-trifluoropropane, 1-Br-4,-fluorobutane, or bromo-trifluoromethane, etc.

The disclosed selective catalytic carbon-carbon coupling reactions may proceed with alkali metal hydroxide MOH (e.g., $M^1$=Li, Na, K), without any additive. Addition of alkali metal oxide $M^2O$ (e.g., $M^2$=Ca) further facilitates mixing of components allowing having a well stirrable reaction mixture at all reaction times resulting in a high yield of product through a metalation chemical process and allowing efficient separation of solution from the solids after the reaction.

In one embodiment, the mono-substituted cyclopentadienes (I) are selectively synthesized in THF from freshly cracked CpH and alkyl halide compound R(Hal) or fluoroalkyl halide compound R(F)(Hal) by using 1.4-1.6 molar excess of CpH relative to R(Hal) or R(F)(Hal) and maintaining a temperature range of 15-40° C. under an atmospheric pressure during the reaction. The selective catalytic carbon-carbon coupling reaction is exothermic, thus cooling of the reaction mixture to room temperature is necessary to maintain a high selectivity of reaction.

The most important key point in the present application is the application of the catalyst which selectively promotes the reaction of the CpH and the alkyl halide R(Hal) or fluoroalkyl halide R(F)(Hal) and allows obtaining the targeted mono-substituted cyclopentadienes (I) in a high yield.

The catalyst may be a tertiary phosphonium salt such as $Bu_4PCl$. The approximate amount of catalyst varies from 0.1 to 10 mol % relative to the amount of R(Hal) or R(F)(Hal), preferably from 2 to 6 mol %. In case applying a catalyst, a conversion rate with a high selectivity is achieved in a temperature range from 0 to 70° C., preferably from 15 to 30° C.

Other catalysts, such as $PPent_4Cl$ (Pent=$C_5H_{11}$), $PPh_4Cl$ (Ph=$C_6H_5$), may be applicable to make the reaction selective. Based on the comparative examples that follow, the reaction has to be performed in the presence of calcium oxide in THF, rather than in water, to have a good yield of the product.

The reaction may proceed until all R(Hal) or R(F)(Hal) are consumed. The degree of conversion may be monitored in-situ by GC, Raman spectroscopy or any other suitable technique. After conversion, all solids are separated by filtration or decantation. After separation of the solids, the remaining liquid may contain the catalyst, unreacted CpH, $Cp_2$ and the solvent. The products include the mono-substituted cyclopentadiene (I), disubstituted cyclopentadiene, trisubstituted cyclopentadiene, which may be separated by distillation, crystallization or filtration processes.

The process of synthesis of the mono-substituted cyclopentadiene (I) may be performed in a batch reactor or in a flow reactor. The optimized selectivity of the process is achieved when approximately 20-400% excess, preferably 40-80% excess of CpH monomer is used relative to R(Hal) or R(F)(Hal).

The excess of CpH monomer should be separated after the reaction by distillation from the reaction product—mono-substituted cyclopentadiene (I). Due to the low boiling point of CpH monomer (i.e., 40.8° C.), it may be separated in the first fraction during the distillation process. The absence of CpH monomer may be confirmed by any suitable analytical methods including proton NMR, gaseous chromatography.

The reaction products may contain cyclopentadiene dimers $Cp_2$ either due to dimerization of the CpH monomer during the catalytic carbon-carbon coupling reaction and distillation of the products after the reaction, or due to the CpH monomer taken for the reaction initially contained some amount of $Cp_2$. The $Cp_2$ may be separated by distillation from the reaction product mono-substituted cyclopentadiene. Alternatively, the mono-substituted cyclopentadiene (I) may be used as a mixture with the $Cp_2$ for further steps without any additional purification. Fractional distillation may proceed below, at room temperature or by moderate heating in a temperature range from −30 to 100° C., preferably from 0 to 40° C. and at various pressure ranges. Ambient or reduced pressure from 0.01 to 760 Torr or from 0.1 to 100 Torr is preferred as it helps to reduce distillation temperature and suppress side reactions such as dimerization of $C_5H_5$—R, which results in a lower yield of the product mono-substituted cyclopentadiene (I).

The mixture of the product mono-substituted cyclopentadiene $C_5H_5$—R (I) with $Cp_2$ obtained after the brief stripping of volatiles from the reaction mixture may be directly reacting with the stoichiometric amount of alkyllithium reagent such as methyllithium MeLi to convert all mono-substituted cyclopentadiene $C_5H_5$—R (I) into the corresponding lithium compound Li($C_5H_4$—R). The relative amount of $Cp_2$ in the mixture of the product mono-substituted cyclopentadiene $C_5H_5$—R (I) with $Cp_2$ obtained after the brief stripping of volatiles from the reaction mixture may vary from 5 to 80% w/w and the solvent may vary from 1% to 50%. The $Cp_2$ and solvent are then removed from Li($C_5H_4$—R) by stripping under the reduced pressure. If the reaction of $C_5H_5$—R and alkyllithium compound is attempted in a non-furan solvent such as diethylether, arenes (toluene, xylene, etc.) and alkanes (pentane, hexane, heptane, etc.), a stable gels and viscous non-stirrable paste is formed. Addition of a furan solvent such as THF, Me-THF (methyl-tetrahydrofurane) prevents the formation of gels and viscous solutions, and the reaction with alkyllithium compound will proceed smoothly, with a good mixing and a high volumetric efficiency. Hence, in one embodiment, a furan solvent, preferably THF, is utilized for the reaction, where the relative amount of solvent in the reaction mixture before addition of alkyllithium reagent is from 20% to 90%. In one embodiment, THF is added to the mixture of the mono-substituted cyclopentadiene (I) and $Cp_2$ before addition of alkyllithium compound to produce the metal Cp complex (II).

The alkyllithium reagent may be a neat or solution of MeLi, n-butyl-lithium, tert-butyl lithium or any other suitable alkyllithium compounds in any suitable solvents, preferably being ether, toluene, xylene, alkane solvent (pentane, hexane, heptane, and octane).

The reaction with the alkyllithium reagent proceeds within the temperatures from −80° C. to room temperature, preferably from −10° C. to 0° C. It is known that a higher temperature favors formation of undesirable side products such as cyclopentadienyl lithium $LiC_5H_5$. After addition of the alkyllithium compound, the reaction mixture is warmed to room temperature forming $Li(C_5H_4$—R), while liberation of gaseous byproducts (such as b-butane, methane) ceases and then all volatiles are stripped under the reduced pressure. The reduced pressure may be from 0.01 Torr to 100 Torr, preferably from 0.1 Torr to 1 Torr.

The residual THF solvent may be removed from $Li(C_5H_4$—R) by heating of $Li(C_5H_4$—R) under reduced pressure up to 220° C., preferably up to 150° C. The reduced pressure may be from 0.01 Torr to 100 Torr, preferably from 0.1 Torr to 1 Torr.

In one exemplary embodiment, when the mono-substituted cyclopentadiene (1) is a 2-pentyl-cyclopentadiene (2-Pent-$C_5H_5$), in a mixture of 2-Pent-$C_5H_5$ with $Cp_2$, the relative amount of the $Cp_2$ in the mixture may vary from 5 to 70% w/w and the solvent may vary from 1% to 30%. The mixture may directly react with the stoichiometric amount of MeLi to convert all 2-Pent-$C_5H_5$ to the corresponding lithium complex Li(Cp-2-Pent). The $Cp_2$ and solvent may be removed from Li(Cp-2-Pent) by stripping under the reduced pressure. The exemplary schematic reaction is presented as follows:

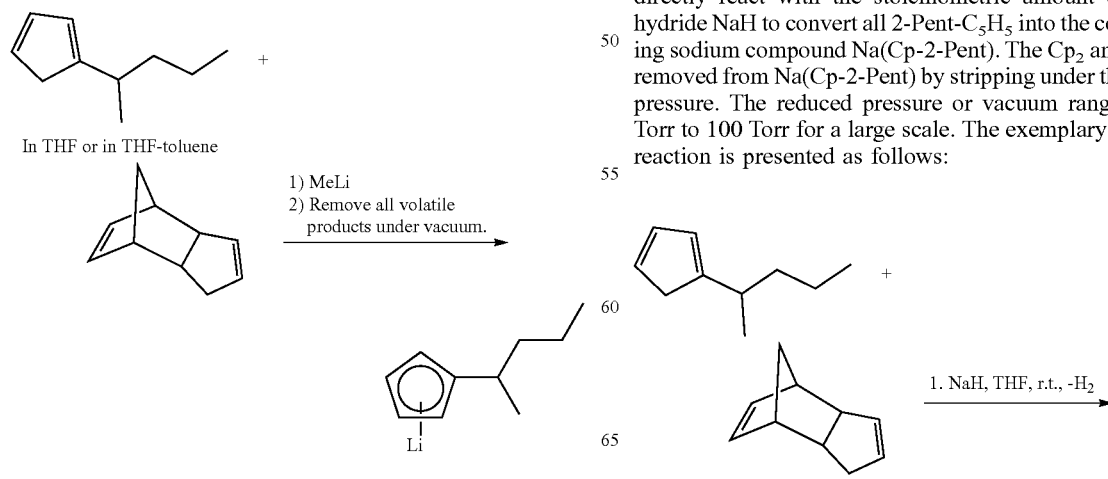

The purity of Li(Cp-2-Pent) is monitored by proton NMR, FTIR, Raman, elemental analyses or any other suitable methods. The purity of Li(Cp-2-Pent) ranges from 90% to 99.99%, preferably from 97% to 99.9%, more preferably from 99% to 99.9%.

The disclosed synthesis method, namely lithiation of the mono-substituted cyclopentadiene (I) in the mixture with $Cp_2$, followed by removal of $Cp_2$ under vacuum, allows preparation of highly pure lithium compound (purity more than 99%), even though the starting compound 2-Pent-$C_5H_5$ was not purified from the examples that follow.

Alternatively, after the synthesis of the mono-substituted cyclopentadiene (I), the volatiles are briefly stripped from the reaction mixture, resulting in the mixture containing 5 to 80% w/w $C_5H_5$—R, 1% to 50% w/w $Cp_2$, and 1% to 50% solvent. This mixture may be directly reacting with the stoichiometric amount, relative to the mono-substituted cyclopentadiene (I), of alkali metal hydride such as NaH, KH to convert all $C_5H_5$—R into the corresponding alkali metal Cp complex $M(C_5H_4$—R) (M preferably Na, K). The $Cp_2$ and solvent are removed from $M(C_5H_4$—R) by stripping under the reduced pressure. In one exemplary embodiment, THF is added to the mixture containing 5 to 80% w/w $C_5H_5$—R, 1% to 50% w/w $Cp_2$, and 1% to 50% solvent before addition of metal hydride.

The metal hydride MH (M is a Group I, Group II or Group II main group metal or a transition metal selected from K, Na, Sr, Ba, Ga, In, Y or Yb) reagent may be a neat or suspension in mineral oil. The reaction with MH proceeds within the temperatures from 0° C. to 50° C., preferably from 20° C. to 30° C., since higher temperatures favors undesirable dimerization of the mono-substituted cyclopentadiene (I). When liberation of hydrogen ceases, all volatiles are stripped under the reduced pressure. The reduced pressure may be from 0.01 Torr to 100 Torr, preferably from 0.1 Torr to 1 Torr.

In one exemplary embodiment, after the synthesis of 2-Pent-$C_5H_5$, in the mixture of 2-Pent-$C_5H_5$ with $Cp_2$, the relative amount of $Cp_2$ dimer may vary 5 to 70% w/w, the THF solvent may vary from 1% to 30%. The mixture may directly react with the stoichiometric amount of sodium hydride NaH to convert all 2-Pent-$C_5H_5$ into the corresponding sodium compound Na(Cp-2-Pent). The $Cp_2$ and THF are removed from Na(Cp-2-Pent) by stripping under the reduced pressure. The reduced pressure or vacuum ranges from 1 Torr to 100 Torr for a large scale. The exemplary schematic reaction is presented as follows:

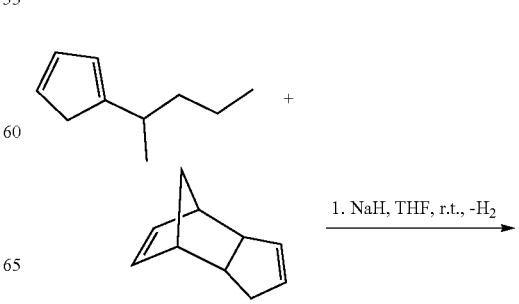

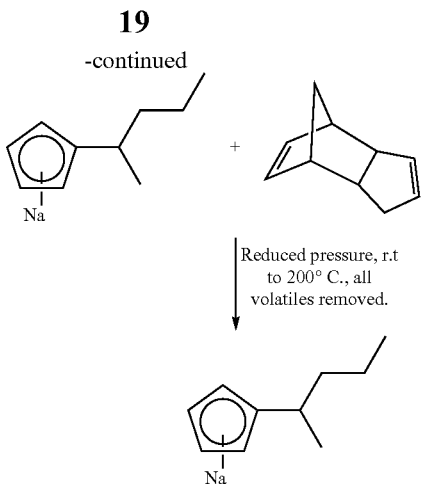

The residual THF solvent may be removed from Na(Cp-2-Pent) by heating under reduced pressure up to 220° C., preferably up to 200° C. The purity of Na(Cp-2-Pent) is tested by proton NMR, FTIR, Raman, elemental analysis or any other suitable methods. The purity of Na(Cp-2-Pent) is from 90% to 99.99% preferably from 97% to 99.9%, more preferably from 99% to 99.9%.

Alternatively, after the synthesis of 2-Pent-$C_5H_5$, in the mixture of 2-Pent-$C_5H_5$ with $Cp_2$, the relative amount of dimer may vary 5 to 70% w/w and the THF solvent may vary from 1% to 30%. The mixture may directly react with the stoichiometric amount of potassium hydride KH to convert all 2-Pent-$C_5H_5$ into the corresponding potassium compound K(Cp-2-Pent). The $Cp_2$ and solvent are removed from K(Cp-2-Pent) by stripping under the reduced pressure. The exemplary schematic reaction is presented as follows:

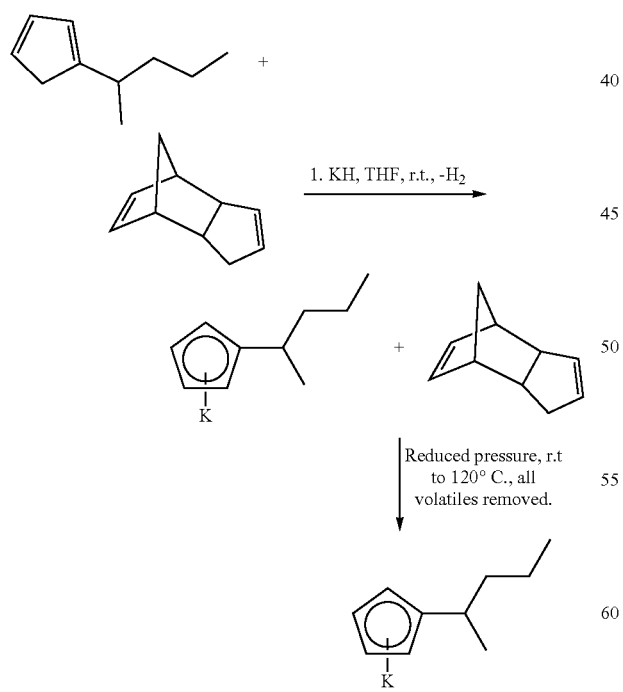

The residual THF solvent may be removed from K(Cp-2-Pent) by heating under reduced pressure up to 150° C., preferably up to 120° C. under stirring. The purity of K(Cp-2-Pent) is tested by proton NMR, FTIR, Raman, elemental analysis or any other suitable methods. The purity of K(Cp-2-Pent) is from 90% to 99.99% preferably from 97% to 99.9%, more preferably from 99% to 99.9%.

Here, the synthesis and separation of the disclosed mono-substituted cyclopentadienes (I) may be performed in a batch reactor comprising of the following steps of:
 a) adding alkali metal hydroxide (e.g., KOH, NaOH), alkaline earth metal oxide (e.g., CaO) and a suitable solvent in a reactor;
 b) adding the cyclopentadiene monomer into the reactor;
 c) charging the reactor with a catalyst with or without a solvent;
 d) stirring the mixture in the reactor with or without cooling to obtain a suspension;
 e) adding R(Hal) or R(F)(Hal) to the suspension to form a solution with cooling to maintain a temperature within a range of from 0 to 70° C. at 1 atm;
 f) separating solids from the solution (with optional filtration) and adding the solution into a separate distillation unit that allows:
  i. isolating the unreacted starting material(s);
  ii. isolating the solvent;
  iii. isolating the reaction product—the mono-substituted cyclopentadiene (I); and
  iv. recovering the solvent (optional);
 g) directing the recovered solvent into the step a);
 h) drying the mono-substituted cyclopentadiene (I) with molecular sieves;
 i) directing the mono-substituted cyclopentadiene (I) to the next step for synthesis of metal Cp complexes (II) or collecting the mono-substituted cyclopentadiene (I) in a suitable containers.

The synthesis and separation of the disclosed metal Cp complexes (II) may be performed in a batch reactor following the formation of the mono-substituted cyclopentadiene (I) comprising of the following steps of:
 j) adding the mono-substituted cyclopentadiene (I) in a reactor;
 k) adding THF into the reactor and cooling the reactor to −20° C., preferably to −5° C. at 1 atm;
 l) adding alkyllithium solution, preferably methyl lithium or butyl lithium solution, or a suspension of MH (M is a Group I, Group II or Group II metal or a transition metal selected from K, Na, Sr, Ba, Ga, In, Y or Ye) in mineral oil or a solid MH, into the reactor, while maintaining the temperature below 5° C., preferably from −5 to 0° C. during the addition of alkyllithium, or maintaining temperature below 40° C., preferably from 20 to 30° C. during the addition of MH;
 m) warming the reaction mixture to room temperature (optional) to form the metal Cp complex (II);
 n) removing all volatiles under a reduced pressure;
 o) heating the obtained metal Cp complex (II) above their melting point under vacuum to remove the residual volatile organic products (optional);
 p) directing the obtained metal Cp complex (II) to the next step (e.g., for preparation of a film deposition precursor) or collecting the obtained metal Cp complex (II) in a suitable container.

FIG. 1 is a diagram of a batch process for catalytic synthesis of a mono-substituted cyclopentadiene (I) and conversion of the mono-substituted cyclopentadiene (I) to a metal Cp complex (II). Although the batch process for synthesis of the mono-substituted cyclopentadiene (I) is preferable to perform under the inert atmosphere such as $N_2$, a noble gas (i.e., He, Ne, Ar, Kr, Xe), it may tolerate some amount of air and water. Starting compounds and solvents are not necessary to purify from water and degas from oxygen, while adding the starting compounds and solvent may be performed on air. More specifically, pot reactor 1 is charged with alkali metal hydroxide (e.g., KOH, NaOH) and alkaline earth metal oxide (e.g., CaO). Solvent 2, preferably tetrahydrofuran (THF), is delivered via line 13 into pot reactor 1. CpH 3 and solution of catalyst 4 are transferred via lines 14 and 15, respectively, into pot reactor 1. Lines 13, 14 and 15 are merged into mixing line 16 that connect to pot reactor 1. Optionally, catalyst 4 is added to pot reactor 1 as a neat compound. Halogen substituted hydrocarbon R(Hal) or halogen substituted hydrofluorocarbon R(F)(Hal) (e.g., 2-Br-pentane) reactant 5 is added to pot reactor 1 via a separate line 17. The starting compounds, e.g., solvent, CpH, catalyst and R(Hal) or R(F)(Hal), may be added to pot reactor 1 by pump (not shown) or by pressure difference. Pot reactor 1 may be a typical vessel with means of agitation, temperature and pressure control and reaction monitoring. Pot reactor 1 has a cooling capability and is maintained at a temperature ranging from approximately −15° C. to approximately 70° C., preferably from approximately 15° C. to room temperature or 35° C. and the corresponding pressure approximately 1 atm. The reaction monitoring is provided by chromatographic (e.g., GC), spectroscopic (e.g., Raman) or any other suitable analytical techniques. The reaction may be performed under 1 atm of nitrogen. After the desired range of conversion of the starting compounds is achieved, preferably when a relative amount of R(Hal) or R(F)(Hal) (e.g., 2-Br-pentane) in the reaction mixture is less than 0.1% according to the analyses of the reaction monitoring, more preferably less than 0.01%, the reaction mixture in pot reactor 1 is filtered with filter 19 (optional, decanted from solids via 19). The filtrate is directed into distillation setup 6 to further isolate the reaction product—mono-substituted cyclopentadiene 8 by stripping of volatile products through line 21 and disposing waste 7 including pot residue and nonvolatile after the distillation through line 20. The distilled solvent may be recycled to solvent 2 through line 26. The reaction product, mono-substituted cyclopentadiene 8, namely, the Mono-substituted cyclopentadiene (I), may be purified to any desirable level, e.g., up to 99.99% (ultra-high-purity (UHP)). The product of lower purity or even the crude reaction mixture without any purification, which contains $Cp_2$, may be utilized to convert the mono-substituted cyclopentadiene (I) to the corresponding metal Cp complexes (II) through a metalation chemical process.

Before the metalation process, the mono-substituted cyclopentadiene 8 is dried with molecular sieves and degassed via line 22. The dried and degassed product 8 is directed into pot reactor 9. Solvent 2 delivered to pot reactor 9 is also dried with molecular sieves through line 18. All of contact components in the pot reactor 9 needs to be air- and moisture-free. Pot reactor 9 may be performed under an inert atmosphere, such as $N_2$, a noble gas (i.e., He, Ne, Ar, Kr, Xe), a combination thereof or any other dry/inert environment. Pot reactor 9 may be a typical vessel with means of agitation, temperature and pressure controls and reaction monitoring. Pot reactor 9 has a cooling capability and is maintained at a temperature ranging from approximately −15° C. to approximately 70° C., preferably from approximately −5° C. to room temperature or 30° C. and the corresponding pressure approximately 1 atm. For example, for MeLi, the temperature range is from −5° C. to 0° C.; for MH (e.g., M=Li, Na, K, Ga, In, Sr, Ba, Y or Yb), the temperature is from 20° C. to 30° C. Pot reactor 9 is connected to a nitrogen line and has capability of venting hydrogen, methane, butane formed in the metalation reaction. Pot reactor 9 has outlet 23 for addition of alkyl lithium solution or solid alkali metal hydrides, e.g., solid addition funnel. After completion of the metalation, the solid product, the metal complexes 12, is obtained through line 24 and the reaction mixture in pot reactor 9 warmed to room temperature and all volatiles are stripped under a reduced pressure via line 25 to receiver 11 where waste is disposed. The reduced pressure ranges from 0.05 to 760 Torr, preferably, from 0.1 to 50 Torr, as it helps to reduce distillation temperature and speed up the distillation process. Optionally, at the last stages of solvent stripping, the obtained metal Cp complex (II) 12 may be melted with stirring under vacuum for full uptake of residual volatile organic species such as $Cp_2$ and THF. For example, THF is fully removed from the sodium complex $Na(C_5H_4-R)$ (further described from the examples that follow, such as Na(Cp-2-Pent) only by heating up to 200° C. and reduced pressure 0.05-1 Torr. The metal Cp complex (II) 12 may be purified to any desirable level, e.g. up to 99.99% (ultra-high-purity (UHP)) by keeping under vacuum, recrystallization or any other suitable means. The product of lower purity, e.g., 90%-99% may be utilized in further metathesis reactions to obtain other metal complexes, e.g., hafnium complex $HfCl_2(Cp-2-Pent)_2$ or indium complex In(Cp-2-Pent).

Yet, alternatively, the synthesis and separation of the disclosed mono-substituted cyclopentadiene (I) may be performed in a flow reactor comprising of the steps of:

a. packing a flow reactor with alkali metal hydroxide (preferably KOH or NaOH) and alkaline earth metal oxide (preferably CaO);

b. preparing a solution of a catalyst in a suitable solvent;

c. mixing R(Hal), cyclopentadiene monomer and solution of the catalyst in the flow reactor;

d. recirculating the reaction mixture containing R(Hal), cyclopentadiene monomer and the catalyst in a suitable solvent through the flow reactor, while monitoring degree of consumption of R(Hal) by any suitable methods (Raman, FTIR spectroscopy, gaseous chromatography, liquid chromatography, proton NMR spectroscopy);

e. when the required degree of conversion is confirmed by analytical methods, delivering the reaction mixture in a crude distillation setup;

f. isolating the product by distillation that allows:
  i) isolating the unreacted starting material(s);
  ii) isolating the solvent;
  iii) isolating the reaction product, the mono-substituted cyclopentadiene (I); and
  iv) recovering the solvent (optional);

g. drying the obtained mono-substituted cyclopentadiene (I) with molecular sieves; and h. directing the mono-substituted cyclopentadiene (I) to the next step for synthesis of the metal Cp complexes (II) or collecting the mono-substituted cyclopentadiene (I) in a suitable containers.

Further steps of synthesis and separation of the disclosed metal Cp complexes (II) from the mono-substituted cyclopentadiene (I) in a flow process are similar to those of the batch process j)-q).

Figure 2:
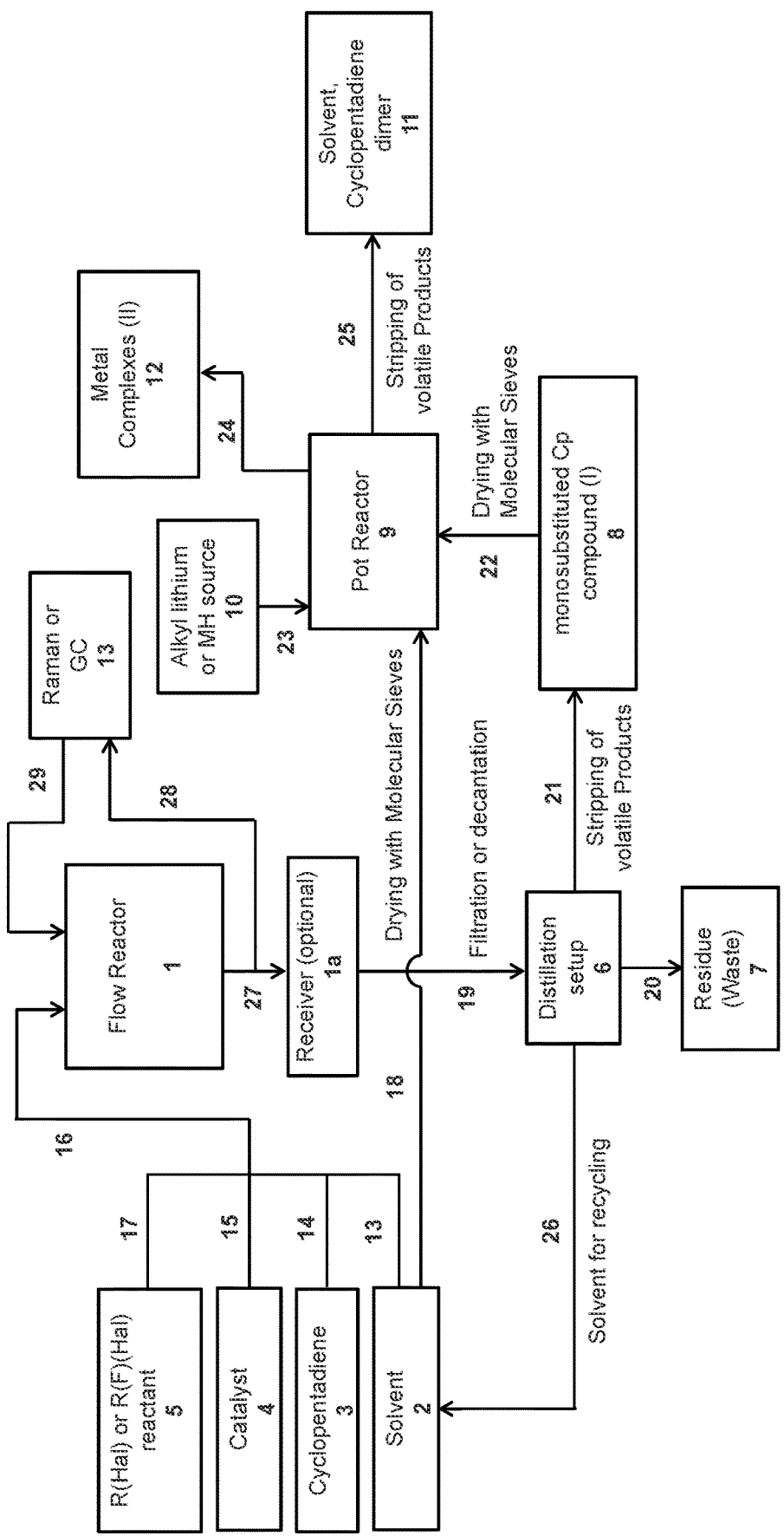
FIG. 2 is a diagram of a flow process for selective catalytic syntheses of the mono-substituted cyclopentadienes (I) and their corresponding metal Cp complexes (II)

FIG. 2 is a diagram of a flow process for catalytic preparation of the mono-substituted cyclopentadiene (I) and the corresponding metal Cp complexes (II). Although the flow process for synthesis of the mono-substituted cyclopentadiene (I) is preferable to perform under the inert atmosphere such as $N_2$, a noble gas (i.e., He, Ne, Ar, Kr, Xe), it may tolerate some amount of air and water and the starting compounds and solvents are not necessary to be purified from water and degased from oxygen, while addition of the starting compounds and solvent may be performed on air. More specifically, flow reactor 1 is packed with alkali metal hydroxide (preferably KOH or NaOH) and alkaline earth metal oxide (preferably CaO). Solvent 2, preferably THF, delivered via line 13 to flow reactor 1. CpH 3 and solution of catalyst 4 are transferred via lines 14 and 15, respectively, into flow reactor 1. R(Hal) or R(F)(Hal) (e.g. 2-Br-pentane) reactant 5 is added to flow reactor 1 via line 17. Lines 13, 14, 15 and 17 are merged into mixing line 16 that connect to pot reactor 1. The starting compounds may be added to flow reactor 1 by pump (not shown) or by pressure difference. Flow reactor 1 may be a tubular reactor with or without inert media such as glass beds or equipped with the pellets of neat alkali metal hydroxide and alkaline earth metal oxide. Flow reactor 1 may be maintained at a temperature ranging from approximately −25° C. to approximately 70° C., preferably from approximately 15° C. to room temperature or 30° C. and the corresponding pressure approximately 1 atm. The temperature selection may depend upon the starting compounds used for synthesis of the mono-substituted cyclopentadiene (I) as well as the target reaction products, that is, the metal Cp complex (II). Flow reactor 1 may be maintained at a pressure ranging from approximately 0.1 atm to approximately 2 atm, preferably approximately at 1 atm. The flow of starting compounds and the reaction mixture in mixing line 16 is selected to provide approximately 5 minutes to approximately 100 minutes of residence time in flow reactor 1, preferably between approximately 5 minutes to approximately 20 minutes residence time. A small part of flow of the reaction mixture after flow reactor 1 is directed to Raman probe or GC chromatograph 13 through line 28 and directed back in to flow reactor 1 through line 29. The reaction mixture is recirculating through flow reactor 1 until R(Hal) or R(F)(Hal) (e.g. 2-Br-pentane) is not fully consumed according to the analysis methods. When a relative amount of R(Hal) or R(F)(Hal) (e.g. 2-Br-pentane) in the reaction mixture is less than 0.1% according to the analysis, preferably less than 0.01%, the reaction mixture is collected in optional receiver 1a through line 27 or directly in the distillation setup 6 through line 19. Receiver 1a may be any sort of trap, including, but is not limited to, dry ice/isopropanol, dry ice/acetone, refrigerated ethanol, and/or liquid nitrogen traps.

The reaction mixtures in receiver 1a may be collected in one or more containers and transported to a new location prior to performance of the next process steps. Alternatively, the reaction product in receiver 1a may be filtered through filter 19 from unreacted solid alkali metal hydroxide, alkaline earth metal oxide, as well as solid reaction byproducts such as potassium bromide (e.g. if KOH and 2-Br-Pentane utilized), and then directed to distillation setup 6 to further isolate the reaction product from any reactants, reaction by-products and solvent. Waste 7 including the nonvolatile residues after the distillation is disposed through line 20, while separated solvent may be recycled through line 26. Further steps are similar to these in the batch process described above.

Synthesis of pure mono-substituted cyclopentadienes (I) may be achieved by hydrolysis of the corresponding metal Cp complexes (II) in the hydrocarbon solvent such as (pentane, hexane, toluene, ether, THF, etc.). The disclosed method, such as hydrolysis of potassium Cp compound K(Cp-2-Pent), produces the pure (i.e., >99%) mono-substituted cyclopentadienes (e.g., $C_5H_5$-2-Pent) in a high yield applying a relatively simple and fast procedure. Potassium salts are very stable compounds and may be shipped to any location or stored for a long time under the nitrogen atmosphere before using it for synthesis, hence this is very convenient starting compound for a simple preparation of pure ligand, especially when the pure mono-substituted cyclopentadiene (I) has boiling point close to that of $Cp_2$ dimer or similar to that of used solvent and could be separated in a pure form by distillation.

The disclosed mono-substituted cyclopentadienes (I) and corresponding metal Cp complexes (II) are intended to be applied to syntheses of metal containing precursors in film forming compositions for film depositions. The alkyl chain of mono-substituted Cp ligand affects the properties of the whole metal containing precursors for the film forming compositions. Specifically, the alkyl chain of mono-substituted Cp ligand will reduce the energy of intermolecular contacts of M(Cp-R) molecules leading to decrease of melting point and increase of volatility of M(Cp-R) precursors (here M is any main Group or transition metal). In the other hand, the fluorine atoms in alkyl chain of $C_5H_5$—R(F) are capable of coordinating to the metal center of M(Cp-R (F)) complexes, coordinately saturate the metal center, thus precluding formation of intermolecular contacts and leading to decrease of melting point and increase of volatility and stability of M(Cp-R(F)) precursors.

In particular, interests are the mono-substituted cyclopentadienes (I) and corresponding metal Cp complexes (II) that have the non-branched and branched alkyl chain R or R(F) containing from three to seven carbon atoms, since this chain length in the ligand may allow to tune the properties of the whole precursors namely improve stability, reduce the melting point and tune the volatility of compound.

Figure 3:
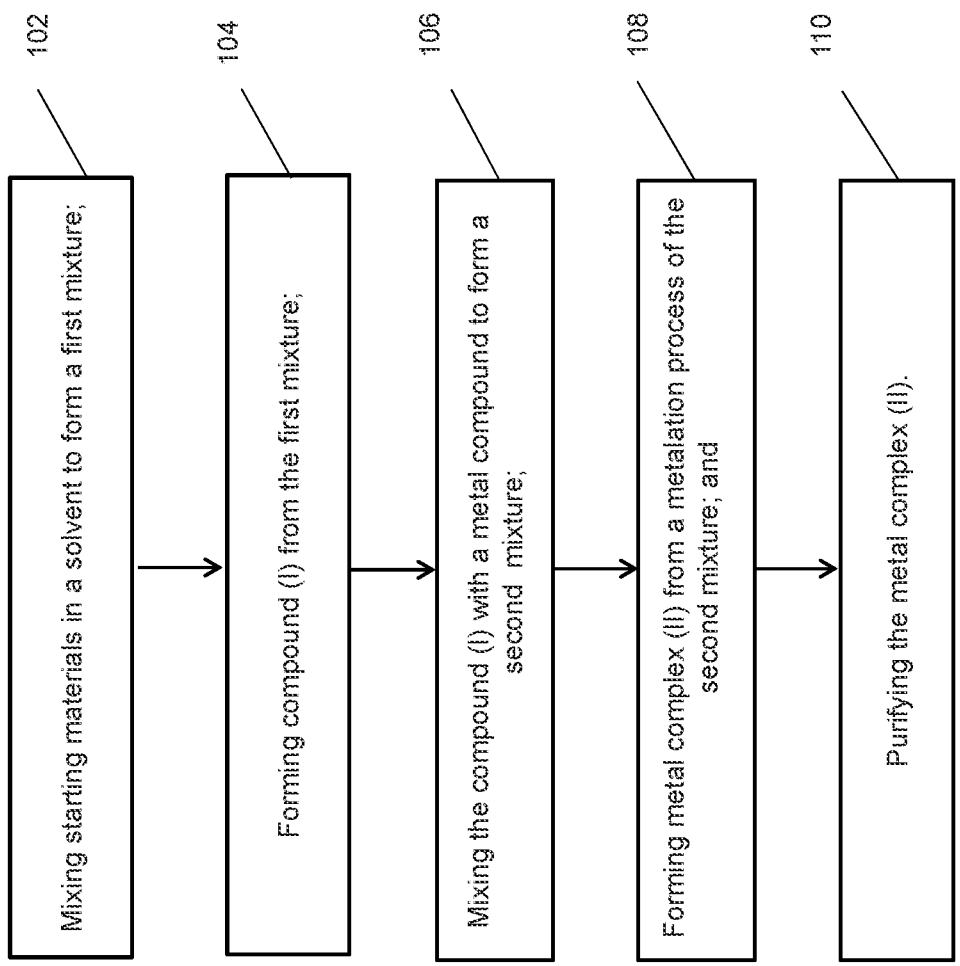
FIG. 3 is a process flowchart for syntheses of the mono-substituted cyclopentadienes (I) and their corresponding metal Cp complexes (II).

The disclosed methods for synthesizing the mono-substituted cyclopentadienes (I) and corresponding metal Cp complexes (II) may be summarized as a flow chart shown in FIG. 3. At Step 102, the starting materials or compounds are mixed in a solvent (e.g., THF) to form a first mixture. The starting materials may include Cp, R(Hal) or R(F)(Hal), MOH (e.g., KOH or NaOH), alkaline earth oxide (e.g., CaO), and a catalyst (e.g., BuPCl). The mono-substituted cyclopentadiene (I) is formed from the first mixture at a temperature ranging from approximately −15° C. to approximately 70° C. under 1 atm at Step 104. In the meantime, $Cp_2$ is also formed along with the formation of the mono-substituted cyclopentadiene (I). In this step, the mono-substituted cyclopentadiene (I) may be or may not be purified to remove unwanted volatile byproducts but the $Cp_2$ may remain in the mixture with the compound (I) due to a similar volatility to that of the mono-substituted cyclopentadiene (I) and will be removed after forming the corresponding metal Cp complex (II). Then the mixture containing mono-substituted cyclopentadiene (I), $Cp_2$ dimer, residual solvents from previous step is mixed with a metal compound, such as an alkyllithium compound (e.g., MeLi) or an alkali metal hydride (e.g., NaH, KH) in a furane solvent such as THF to form a second mixture at step 106. In the presence of the $Cp_2$, in the furan solvent, the corresponding metal Cp complex (II) is formed through a metalation reaction at step 108. In this step, the second mixture may be handled by separation of solids, CpH, part of solvent, multi-substituted cyclopentadienes, etc. At step 110, volatile byproducts including $Cp_2$ are removed under the reduced pressure or vacuum and a pure product of the metal Cp complex (II) is obtained at a temperature ranging from approximately −15° C. to approximately 200° C. Thus, following the above steps, a pure metal Cp complexes (II)

will be obtained even if the synthesized mono-substituted cyclopentadiene (I) was not purified and in a mixture with $Cp_2$ and solvent.

The advantages of the disclosed synthesis methods are as follows.
- a) All starting compounds are stable in air and can be operated at ambient conditions thus reducing costs associated with the degassing, drying of solvents and associated with operations with air sensitive and toxic compounds such as ammonia, $CaH_2$, $CaC_2$, CpNa or Cp(MgCl). Labor intensive and dangerous preparation of CpNa or Cp(MgCl) are excluded.
- b) All starting compounds, except of CpH monomer are widely available commercially and inexpensive. CpH monomer can be easily obtained from a widely available $Cp_2$ dimer.
- c) Synthesis of the mono-substituted cyclopentadiene (I) proceeds at conditions close to ambient and tolerates air ingress.
- d) The reaction mixture after the synthesis of the mono-substituted cyclopentadiene (I) does not require a deep purification before the next metalation step. Any special and expensive purification methods such as chromatography are not required.
- e) The mixture containing the mono-substituted cyclopentadiene (I) can be metalized to produce the metal Cp complexes (II) with the commonly available alkali metal hydrides or alkyl lithium compounds at conditions close to ambient. Dangerous operations with molten alkali metals are excluded.
- f) Purification of the reaction mixture containing metal Cp complexes (II) is straightforward and consists of volatilities stripping. Any special and expensive purification methods such as chromatography or fractional crystallizations are not required.

To our knowledge, the disclosed mono-substituted cyclopentadiene $C_5H_5$—R or $C_5H_5$—R(F) (I) and/or the corresponding metal Cp complex M(Cp-R) or M(Cp-R(F)) (II) have never been synthesized using the disclosed selective catalytic carbon-carbon coupling synthesis methods and have never been disclosed as key components for producing film forming precursors or film forming compositions.

EXAMPLES

The following non-limiting examples are provided to further illustrate embodiments of the invention. However, the examples are not intended to be all-inclusive and are not intended to limit the scope of the inventions described herein.

Experimental Procedure

Starting materials, solvents, reaction mixtures, and products were analyzed by any suitable means, such as by gas chromatography (GC) equipped with Thermal Conductivity Detector (TCD), NMR, Raman spectroscopy using part of the stream or aliquots. All measurements were performed for samples in the closed flask or quartz cell without any contact with the atmosphere.

$Cp_2$ ($C_{10}H_{12}$) cracking was performed under 1 atm of nitrogen applying a commonly used apparatus consisting of parent flask equipped with stirring bar, 20-30 cm Vigreux column, adapter and receiving flask. The apparatus connected to the bubbler under one atm of nitrogen. For cracking, the pot with cyclopentadiene dimer heated above 140° C. (range 140-190° C.) and the cracked CpH monomer collected in receiver cooled with dry ice. The collected monomer was analyzed by GC each time right after cracking. Relative amount of dimer varied from 17% to 46% in cracked product from cracking to cracking according to GC. The cracked product stored in dry ice at all time before the next step. For synthesis of mono-substituted cyclopentadienes, the amount of the cracked fraction was recalculated according to GC data to have the targeted amount of $C_5H_5$ monomer.

The following comparative examples 1 and 2 illustrate that the existing synthesis methods are not applicable for synthesis of mono-substituted cyclopentadienes.

Comparative Example 1. Synthesis of $C_5H_5$-2-Pent

According to the reaction disclosed in WO9742151, KOH in water (371.8 g, 3250.0 mmol, 60% w/w) was added in a 500 mL flask. Then $[Me_3N(C_{16}H_{33})]Cl$ (10 g, 31.25 mmol), CpH monomer ($C_5H_5$ 8.85 g, 133.9 mmol), 2-Br-Pentane ($C_5H_{11}Br$, 25.75 g, 170.5 mmol) were introduced into the flask in turn under stirring. The reaction mixture became a two-phase system containing liquid aqueous phase and viscous organic phase. The mixture was stirred 3 hours at room temperature and then a sample of organic phase is taken for analysis in THF in GC chromatograph. GC results: THF 72.57%, 2-Br-pentane 14.79%, $C_5H_5$-2-Pent 3.07%, $Cp_2$ dimer 5.31%, di-substituted ligand $C_5H_5$-(2-Pent)$_2$ 3.66%, trisubstituted ligand $C_5H_5$-(2-Pent)$_3$ 0.16%. Here are the structural formula of di-substituted ligand $C_5H_5$-(2-Pent)$_2$ (mixture of isomers)

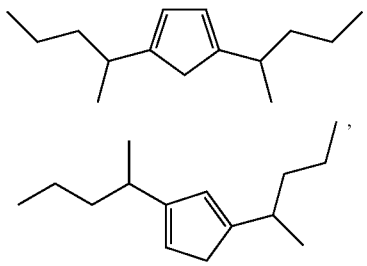

trisubstituted ligand $C_5H_5$-(2-Pent)$_3$ (mixture of isomers, one is shown)

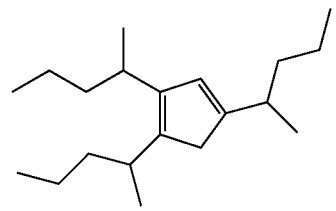 [SMILES: CCCC(C)C1=CC(C(C)CCC)=C(C(C)CCC)C1]

and $Cp_2$ dimer.

A comparison of relative amounts of starting compounds in WO9742151 and in this application are shown in Table 1.

TABLE 1

Relative amounts of starting compounds.

| Method | NaOH | Conc. in $H_2O$ | Aliquat-336 | CpH | 2-Br-pentane |
|---|---|---|---|---|---|
| WO9742151 | 27.4 g | 50% | 0.19 g | 1 | 2.5 g |
| This application | 24.3 g (KOH) | 60% | 0.23 g $[Me_3N(C_{16}H_{33})]Cl$ | 1 | 1.3 g |

[Me$_3$N(C$_{16}$H$_{33}$)]Cl is taken for this application instead of Aliquiat-336. The difference between two tertiary ammonium salts Aliquiat-336 (tricaprylmethylammonium chloride, [Me$_3$NR]Cl, R=C$_8$H$_{17}$ to C$_{10}$H$_{21}$, CAS: 63393-96-4) and [Me$_3$N(C$_{16}$H$_{33}$)]Cl (CAS: 112-02-7) is only 5-7 carbon atoms in long alkyl chain and hence it is assumed that the catalytic properties of two surfactants are close to each other.

Although the mono-substituted cyclopentadiene C$_5$H$_5$-2-Pent and multi-substituted cyclopentadienes C$_5$H$_5$-(2-Pent)$_n$ (n=2,3) are formed in reaction, the mono-substituted cyclopentadiene is difficult to be separated from the reaction mixture.

Comparative Example 2. Synthesis of C$_5$H$_5$-2-Pent

According to the reaction disclosed by Mironov et. al. (Izvestiya Vysshikh Uchebnykh Zavedenii, Khimiya i Khimicheskaya Tekhnologiya (1983), 26(6), 759-761), KOH in water (2a) or solid (2b) (amounts in Table 2, reaction 2a and 2b added in 500 mL flask. THF, CpH monomer, 2-Br-Pentane were introduced into the flask in turn under stirring. The reaction mixture stirred 3 hours at room temperature and then an aliquot of organic phase was taken for analysis, and injected in GC chromatograph.

Reaction 2a, GC results: CpH (0.6%) THF (77.2%), 2-Br-pentane (17.4%), Cp$_2$ dimer (4.8%). Any coupling product including C$_5$H$_5$-2-Pent was not detected in GC.

Reaction 2b, GC results: CpH (2.3%) THF (77.5%), 2-Br-pentane (16.5%), Cp$_2$ dimer (3.2%). Any coupling product including C$_5$H$_5$-2-Pent was not detected in GC.

The product mono-substituted cyclopentadiene C$_5$H$_5$-2-Pent was not detected in GC with solid KOH or KOH solution in water. Hence either water reactive solids such as CaC$_2$ or CaH$_2$ or liquid ammonia solvent is needed to facilitate the reaction according to the recipe from Mironov et. al.

TABLE 2

Relative amounts of starting compounds.

Reaction 2a

|  | KOH 60% w/w in water | CpH (C$_5$H$_6$) | 2-Br-Pentane |
|---|---|---|---|
| g | 19.6 | 1.71 | 5.37 |
| Mmol | 209.5 | 26.3 | 35.6 |

Reaction 2b

|  | KOH solid | CpH (C$_5$H$_6$) | 2-Br-Pentane |
|---|---|---|---|
| g | 17.7 | 2.04 | 5.38 |
| Mmol | 316.0 | 31.3 | 35.6 |

Example 1. Synthesis of C$_5$H$_5$-2-Pent

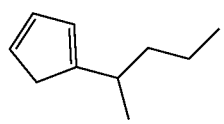

The differences between Example 1 and Comparative Example 2 are: a) addition of a catalyst (to promote the reaction at ambient conditions); b) excess of cyclopentadiene monomer (utilized to achieve a higher selectivity).

KOH (24 g, 209.5 mmol) and CaO (5.6 g, 100 mmol) were first introduced in a flask and then THF (40 mL), CpH (6.33 g, 53.5 mmol, 55% w./w. in the cracked fraction), 2-Br-pentane (5.36 g, 35.5 mmol) and Bu$_4$PCl (1 g, 3.4 mmol) were added into the flask in turn under stirring. The reaction mixture stirred 2 h at room temperature and then analyzed by GC.

GC results: CpH (1.0%) THF (71.9%), C$_5$H$_5$-2-Pent (14.0%), Cp$_2$ dimer (12.6%), C$_5$H$_5$-(2-Pent)$_2$ isomers (0.2% & 0.3%).

Mass spectrum of C$_5$H$_5$-2-Pent. m/z=136 [M]$^+$ (C$_{10}$H$_1$B) (25%), 121 [M-Me]$^+$ (5%), 107 [M-Et]$^+$ (10%), 94 [M-C$_3$H$_6$]$^+$ (60%), 93 [M-C$_3$H$_7$]$^+$ (100%), 91 [M-C$_3$H$_7$-2H]$^+$ (60%), 79 [M-C$_4$H$_9$]$^+$ (40%), 77 [M-C$_4$H$_{11}$]$^+$ (45%), 65 [M-C$_5$H$_{11}$]$^+$ (15%). Observed patterns for cations in mass spectrum are similar to calculated ones.

Example 2. Scale-Up Synthesis of C$_5$H$_5$-2-Pent

The reaction setup included a 5 L flask equipped with an overhead stirrer, thermocouple and dropping funnel. The flask had a possibility of cooling either through a jacketed flask connected to a chiller or a flask immersed in a secondary container, where the cooling agent may be added. The flask was connected to a nitrogen line, purged with nitrogen and kept under 1 atm of N$_2$. KOH (700 g, 10.6 mol) was added in the flask, then CaO (300 g, 5.3 mol), THF (1400 g) and TBPC (30 g) (TBPC refers to tetrabutylphosphonium chloride) were added into the flask in turn using a funnel. Then the content of flask was cooled to nearly 0-5° C. under stirring. Then the cold product of Cp$_2$ cracking containing CpH monomer (500 g, 6.15 mol CpH, 80% of monomer (GC) in a cracked product, and the cracked product kept in dry ice at all time after cracking) is poured in the flask under stirring.

2-Br-pentane (601 g, 3.98 mol, the molar ratio 2-Br-pentane:CpH=1:1.54) was separately weighted and placed in the dropping funnel (operation may be done in air). 2-Br-pentane was added to the reaction mixture in the flask with the speed 10-20 mL/min, while cooling the reaction mixture and maintaining the temperature of reaction mixture within 20-30° C. After all 2-Br-pentane was added, cooling was necessary for some time (approximately 1 h) to have the temperature of reaction mixture within 20-30° C. After that, while the temperature started to decrease at the given degree of cooling, the cooling was stopped and the reaction mixture was allowed to proceed with stirring for approximately 1.5 h at room temperature. Then an aliquot of reaction mixture was taken and analyzed by GC. If 2-Br-pentane was absent on GC (or <0.1% by GC), filtration of reaction mixture could be performed. If 2-Br-pentane was present on GC (>0.1%), the reaction mixture was continuously stirred for 1-1.5 h more at room temperature and reanalyzed by GC. When 2-Br-pentane was absent, the reaction mixture was filtered through the medium glass frit (or alternatively decanted from solids). The remaining solid in the flask and solid on the filter was washed with several portions of THF. All THF filtrates were combined and the flask with the filtered reaction mixture equipped with the stirring bar was connected to the short path distillation setup. The stirring was started in the flask with THF filtrate, dry ice/IPA placed in condenser and a receiving flask was cooled with dry ice (dry ice/IPA). The liquid nitrogen trap may be optionally installed after the receiving flask and before the vacuum line to prevent the contamination of vacuum pump with organic compounds. The short path distillation proceeded under the reduced pressure, while the flask with the filtered reaction mixture (hereinafter "parent flask") was under stirring, and the parent flask was moderately heated to facilitate the distillation (the temperature of liquid in the parent flask is below 0° C. at all times). When almost all THF was stripped, temperature in the parent flask starts quickly rise (e.g. from −15° C. to approximately 0-5° C. at 1-3 Torr Vacuum in the line), and vacuum improves. At this point heating of the parent flask was stopped, and the assembly was filled with 1 atm of nitrogen (or helium or argon), then the receiving flask with THF and CpH monomer was disconnected. The empty parent flask was reconnected to the receiving flask and cooled with dry ice. Then stripping of volatiles from the parent flask proceeds under vacuum until the temperature of liquid in the parent flask reached room temperature and vacuum was at the millitorr range (e.g. 20° C. at 80-150 mTorr in Vacuum line). At this point distillation almost stopped and the system was filled with 1 atm of nitrogen. Then an aliquot of stripped fraction was taken from the receiving flask for GC analysis. Then the receiving flask was disconnected under the nitrogen stream and the freshly regenerated molecular sieves were added to the liquid in the receiving flask (this operation may be performed in the nitrogen purged glove bag or inside the glove box). After addition of molecular sieves the receiving flask with solution of $C_5H_5$-2-Pent was kept in the freezer below −20° C. until the further step. In one experiment, 544.6 g of crude product from the given amounts of starting compounds was obtained. GC results of the product: CpH 1.0%, THF 3.4%, $C_5H_5$-2-Pent 78.2%, $Cp_2$ 16.9%, $C_5H_5$-(2-Pent)$_2$ 0.4%. CpH may be from pyrolysis of $Cp_2$ dimer in GC inlet T=180° C. Yield of $C_5H_5$-2-Pent from 2-Br-Pentane was 77%.

Example 3. Synthesis of $C_5H_5$-2-$C_4H_9$

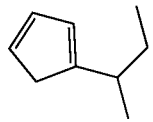

Similar to Example 2, 2-Br-Butane was fully consumed in 4 hours (GC). KOH (140 g, 2.1 mol), CaO (60 g, 1.1 mol), THF (300 mL), TBPC (6 g, 0.02 mol) were taken in turn into a flask. The product of $Cp_2$ cracking contained CpH monomer (122 g, 1.48 mol CpH, 80% of monomer (GC) in cracked product), 2-Br-butane (120.8 g, 0.88 mol, the molar ratio 2-Br-butane:CpH=1:1.67). 182.1 g of crude product after stripping containing 46.8% of $C_5H_5$-2-$C_4H_9$ was obtained. Yield of $C_5H_5$-2-$C_4H_9$ was 79% from 2-Br-butane.

GC results of the crude product: CpH 0.5%, THF 39.9%, $C_5H_5$-2-$C_4H_9$ 46.8%, $Cp_2$ 12.0%, $C_5H_5$-(2-$C_4H_9$)$_2$ 0.6%, {H(2-$C_4H_9$)}$_2$ 0.2%. CpH may be from pyrolysis of $Cp_2$ dimer in the GC inlet T=180° C. Mass spectrum of $C_5H_5$-2-$C_4H_9$. m/z=122 [M]$^+$ ($C_9H_{14}$) (40%), 107 [M-Me]$^+$ (12%), 105 [M-Me-2H]$^+$ (5%), 93 [M-Et]$^+$ (100%), 91 [M-$C_2H_6$-H]$^+$ (70%), 79 [M-$C_3H_7$]$^+$ (20%), 77 [M-$C_3H_9$]$^+$ (50%), 65 [M-$C_4H_9$]$^+$ (15%).

Example 4. Synthesis of $C_5H_5$-1-F-Bu

This new molecule $C_5H_5$-1-F-Bu or $C_5H_5$-1-F—$C_4H_{10}$ was prepared similar to Example 2. 1-F-4-Br-Butane was fully consumed in 3 hours (GC). KOH (6.57 g, 117.1 mmol), CaO (2.86 g, 51.0 mol), THF (35 g), TBPC (0.29 g, 1.0 mmol) were taken, the product of $Cp_2$ cracking contained CpH monomer (4.38 g, 53.0 mmol CpH, 80% of monomer (GC) in cracked product), 1-F-4-Br-butane (4.54 g, 29.3 mmol, the molar ratio 2-Br-butane:CpH=1:1.81). 9.92 g of a crude product after stripping, containing 2.55 g of $C_5H_5$-1-F-Bu was obtained. Yield of $C_5H_5$-1-F-Bu is 62% from 1-F-4-Br-Butane.

GC results of the crude product: CpH 1.0%, THF 65.4%, $C_5H_5$-1-F-Bu 25.7%, $Cp_2$ 7.4%, $C_5H_5$-(1-F—$C_4H_{10}$)$_2$ 0.2%, CpH may be from pyrolysis of $Cp_2$ dimer in the inlet T=180° C.

Mass spectrum of $C_5H_5$-1-F-Bu. m/z=140 [M]$^+$ ($C_9H_{13}$F) (30%), 93 [M-$CH_2CH_2$F]$^+$ (20%), 91 [M-$C_2H_6$F]$^+$ (20%), 80 [M-$C_3H_5$F]$^+$ (40%), 79 [M-$C_3H_6$F]$^+$ (100%), 77 [M-$C_3H_8$F]$^+$ (50%), 66 [$C_5H_6$]$^+$ (15%), 65 [$C_5H_5$]$^+$ (5%).

Example 5. Synthesis of $C_5H_5$-1,1,1-3F—$C_4H_6$

$C_5H_5$-1,1,1-3F—$C_4H_6$ or $C_5H_5$-1,1,1-3F—$C_4H_6$ was prepared similar to Example 2. 1-Br-4,4,4-F-Butane was fully consumed in 3 hours (GC). KOH (19.87 g, (85%), 0.30 mol), CaO (7.77 g, 0.14 mol), THF (111 g), TBPC (1.70 g, 5.77 mmol) were taken. A product of $Cp_2$ cracking containing CpH monomer (19.25 g, 0.23 mol CpH, (80% of monomer (GC) in cracked product)), 1-Br-4,4,4-F-Butane (24.05 g, 0.13 mol, the molar ratio 2-Br-butane:CpH=1:1.85). 17.59 g of crude product containing 7.92 g of $C_5H_5$-1,1,1-3F—$C_4H_6$ after fractional distillation via the short path was obtained. Yield of $C_5H_5$-1,1,1-3F—$C_4H_6$ is 35% from 1-Br-4,4,4-F-Butane in the fraction.

GC results of the crude product: CpH 1.2%, THF 34.2%, $C_5H_5$-1,1,1-3F—$C_4H_6$ 44.4%, $Cp_2$ 18.2%, $C_5H_5$-(1,1,1-3F—$C_4H_6$)$_2$ 1.5%, $C_5H_5$-(1,1,1-3F—$C_4H_6$)$_3$ 0.23% CpH may be from pyrolysis of $Cp_2$ dimer in the GC inlet T=180° C.

Mass spectrum of $C_5H_5$-1,1,1-3F—$C_4H_6$. m/z=176 [M]$^+$ ($C_9H_{11}F_3$) (30%), 137 [M-HF$_2$]$^+$ (1%), 109 (1%) [$C_4H_4F_3$]$^+$, 105 (1%) [$C_8H_9$]$^+$, 93 [M-$CH_2CF_3$]$^+$ (12%), 91 [M-$CH_2CF_3$-$H_2$]$^+$ (15%), 79 [M-$C_3H_4F_3$]$^+$ (100%), 77 [$C_6H_5$]$^+$ (50%), 69 [$CF_3$]$^+$ (5%), 65 [$C_5H_5$]$^+$ (50%).

Example 6. Synthesis of Li(Cp-2-Pent)

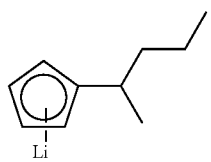

This new molecule Li(Cp-2-Pent) or Li(Cp-2-$C_5H_{11}$) was prepared with a crude product of C—C coupling reaction (166.6 g of 70.6% w/w solution, 0.86 mol $C_5H_5$-2-Pent) and 247.6 g of THF were placed under nitrogen in 2 L flask equipped with the thermocouple, stirring bar and connected to the nitrogen line under 1 atm of nitrogen. The flask with solution was cooled and maintained in the range −10 to 0° C. Separately other 1 L Schlenk flask was filled with MeLi solution in ether (540 mL of 1.6 M solution, 0.86 mol) under nitrogen, and then MeLi solution was added via cannula to the flask with stirred solution of $C_5H_5$-2-Pent in THF, while maintaining temperature in the range −5 to 5° C. After all MeLi was added, the content of flask was allowed to warm to room temperature under stirring. When no more gas liberation was observed at room temperature, the trap was installed between the flask and the vacuum line. The trap was vacuumed and immersed in liquid nitrogen and all solvents were removed in the liquid nitrogen trap. At the certain moment, when almost all solvents were removed, the content turned into a fluffy solid, which started melting to a viscous glassy solid at about 100° C. with liberation of significant amount of volatile organic species. All volatiles were removed from the solid by heating under vacuum. In some experiments heating under vacuum to 150-180° C. was necessary to remove all volatile organic species from bulk Li(Cp-2-Pent). Then the pot content was cooled under dynamic vacuum to nearly room temperature and the flask was transferred in a glove box, and the content analyzed. Yield of Li(Cp-2-Pent) was 120.0 g, 98% from $C_5H_5$-2-Pent. M.P. 96° C. (DSC) producing a viscous paste, phase transition to liquid was at 202° C. (DSC). $^1$H NMR (THF-d8): 5.48 (s, 4H, $C_5H_4$), 2.57 (sext, 1H, $CH_2CHMe$), 1.58 (m, 1H, $CH(CH_2)_2Me$), 1.39 (m, 3H, $CH(CH_2)_2Me$), 1.20 (d, 3H, CH-Me), 0.90 (t, 3H, $CH_2$-Me). Purity according to $^1$H NMR was 99.5%. Assignment and relative amount of impurities was based on chemical shifts and total intensities of resonances. Representative amount of impurities for the given procedure: $C_5H_5$-2-Pent 0.25%, other impurities in total 0.25%. Li(Cp-2-Pent) may contain Li(Cp-3-$C_5H_{11}$) if starting 2-Br-Pentane contains 3-Br-Pentane. Li(Cp-2-Pent) is a brand new compound (CAS No: 2413046-23-6).

Example 7. Synthesis of Li(Cp-2-$C_4H_9$)

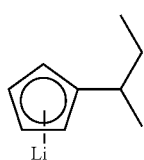

Li(Cp-2-$C_4H_9$) or Li($C_5H_5$-2-$C_4H_9$) was synthesized similar to Example 6. 177.5 g of crude product of C—C coupling reaction (46.8% w/w solution, 0.68 mol. Cp-2-$C_4H_9$), 425.2 mL of 1.6 M solution of MeLi in $Et_2O$ (0.68 Mol) and 300 g of THF were taken. Gelation observed at lower amount of THF. The reaction product heated up to 65° C. under vacuum after the reaction. The yield is 88 g, quantitative from $C_5H_5$-2-$C_4H_9$. $^1$H NMR (THF-d8): 5.50 (m, 4H, $C_5H_4$), 2.54 (sext, 1H, $CH_2CHMe$), 1.63 (m, 1H, $CH(CH_2)_2Me$), 1.47 (m, 1H, $CH(CH_2)_2Me$), 1.21 (d, 3H, CH-Me), 0.91 (t, 3H, $CH_2$-Me). Purity according to $^1$H NMR was 98%, relative amount of coordinated THF 0.4%, Cp dimer 0.2%. M.P was 193° C. (DSC). Note: overheating of reaction mixture during the MeLi addition was leading to appearance CpLi impurity; insufficient amount of THF was leading to gelation resulting in incomplete reaction, residual MeLi in sample, local overheating resulting in appearance of CpLi impurity.

Example 8. Synthesis of K(Cp-2-Pent)

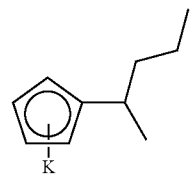

This new molecule K(Cp-2-Pent) or K(Cp-2-$C_5H_{11}$) was prepared with the crude product of C—C coupling reaction (475 g of 60.3% solution in THF, 2.10 mol of $C_5H_5$-2-Pent and anhydrous THF (506 g) placed under nitrogen in 3 L three necked flask equipped with the stirring bar and thermocouple. The flask was connected to the vacuum/nitrogen line and was under 1 atm of nitrogen. Separately, solid KH (84.3 g, 2.1 mol) was added in the solid addition funnel under nitrogen (e.g. in glove box). The solid addition funnel was connected to the flask under the flow of $N_2$. KH was then added by portions via the solid addition funnel to the stirred THF solution of cyclopentadiene ligand to maintain steady hydrogen liberation, while temperature of THF solution was maintained below 30° C. by any suitable means of cooling. After all KH was added, the reaction mixture was stirred until hydrogen liberation was ceased (approximately 2-3 hours at room temperature). Then the solid addition funnel was disconnected under $N_2$ flow and all volatiles are stripped under vacuum. At the end of distillation, the residue in the flask was heated to 100-130° C. and kept under vacuum under stirring until liberation of gaseous product ceases (vacuum in the line improves and reaches its baseline value). At that time, heating was shut off and the parent flask was cooled to nearly room temperature, transferred in the glove box and the content analyzed. For the given amount of KH, 347.6 g (1.99 mol) of K(Cp-2-Pent) was isolated, corresponding to the yield 94.9%. M.P of K(Cp-2-Pent) 55-56° C. (DSC). $^1$H NMR (THF-d8): 5.36 (2H, $C_5H_4$), 5.32 (2H, $C_5H_4$), 2.57 (sext, 1H, $CH_2CHMe$), 1.58 (m, 1H, $CH(CH_2)_2Me$), 1.44 (m, 1H, $CH(CH_2)_2Me$), 1.31 (m, 2H, $CH(CH_2)_2Me$), 1.10 (d, 3H, CH-Me), 0.98 (t, 3H, $CH_2$-Me). Purity according to $^1$H NMR was 99.9%. Assignment and relative amount of impurities was based on chemical shifts and total intensities of resonances. Representative amount of impurities for the given procedure: $C_5H_5$-2-Pent 0.10%. K(Cp-2-Pent) may contain K(Cp-3-Pent) if starting 2-Br-Pentane contains 3-Br-Pentane. Since K(Cp-2-Pent) is air and moisture sensitive, the synthesis process was done under the inert atmosphere.

Example 9. Synthesis of K(H(Cp-1-F-Bu)

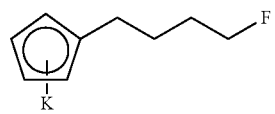

This new molecule K(H(Cp-1-F-Bu K(H(Cp-1-F-Bu) prepared similar to that described in Example 8. 7.5 g of crude product of C—C coupling reaction (40.3% w/w solution, 22.1 mmol. $C_5H_5$-1-F-Bu, 1.2 g (29.9 mmol) of solid KH and 45 g of THF were taken. KH to solution of $C_5H_5$-1-F-Bu was added by cooling, keeping the temperature of reaction mixture below room temperature. After solvent stripping, the reaction product heated up to 40° C. under vacuum. Yield 3.99 g, quantitative from $C_5H_5$-1-F-Bu. $^1$H NMR (THF-d8): 5.37 (m, 4H, $C_5H_4$), 4.54 (t, 1H, $CH_2F$), 4.45 (t, 1H, $CH_2F$), 2.51 (m, 2H, $CH_2CH_2F$), 1.79 (m, 2H, $CH_2CH_2CH_2$), 1.61 (m, 2H, Cp-$CH_2$), overlapped with resonance of THF from solvent. Compound contains 3 mol. % of THF. Purity of $K(THF)_{0.03}$(Cp-BuF) from $^1$H NMR was 96.8% w/w, relative amount of Cp dimer 0.4% w/w, CpK 2.9% w/w. M.P=89-91° C. with decomposition (DSC).

Example 10. Synthesis of K(Cp-1,1,1-3F-Bu)

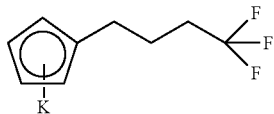

Preparation was similar to that described in Example 9. 17.6 g of crude product of C—C coupling reaction (45% w/w solution, 45 mmol. $C_5H_5$-1,1,1-3F-Bu, 2.0 g (50 mmol) of solid KH and 40 g of THF were taken. KH to solution of $C_5H_5$-1,1,1-3F-Bu was added by cooling, keeping the temperature of reaction mixture below room temperature. After solvent stripping, the reaction product heated up to 50° C. under vacuum. Yield of K(Cp-1,1,1-3F-Bu) was 10.32 g, quantitative from $C_5H_5$-1,1,1-3F-Bu. $^1$H NMR (THF-d8): 5.40 (m, 4H, $C_5H_4$), 2.57 (t, 2H, $CH_2CF_3$), 2.24 (m, 2H, $CH_2CH_2CF_3$), 1.80 (m, 2H, Cp-$CH_2$) overlapped with resonance of THF. Compound contains 4 mol. % of THF. Purity of $K(THF)_{0.04}$(Cp-BuF$_3$) according to $^1$H NMR was 96.4% w/w, relative amount of Cp dimer 0.4% w/w, CpK 3.3% w/w. M.P. 105° C., decomposition from 155° C. (DSC).

Example 11. Synthesis of Na(Cp-2-Pent)

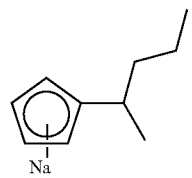

This new molecule Na(Cp-2-Pent) or Na(Cp-2-$C_5H_{11}$) was prepared similar to that of K(Cp-2-Pent) (Example 8). THF from Na(Cp-2-Pent) could be fully removed by heating at 150-200° C. with stirring under vacuum. Yield: 95.8% for 160 g scale; M.P. 110° C. (DSC); $^1$H NMR (THF-d8): 5.51 (d, 4H, $C_5H_4$), 2.64 (sext, 1H, $CH_2CHMe$), 1.58 (m, 1H, $CH(CH_2)_2Me$), 1.40-1.20 (m, 3H, $CH(CH_2)_2Me$), 1.17 (d, 3H, CH-Me), 0.92 (t, 3H, $CH_2$-Me). Purity according to $^1$H NMR was 99.6%. Assignment and relative amount of impurities was based on chemical shifts and total intensities of resonances. Representative amount of impurities for the given procedure $C_5H_5$-2-Pent 0.20%, other impurities in total 0.2%. Na(Cp-2-Pent) may contain Na(Cp-3-$C_5H_{11}$) if starting 2-Br-Pentane contains 3-Br-Pentane.

Example 12. Synthesis of Pure (>99%) $C_5H_5$-2-Pent from Hydrolysis of K(Cp-2-Pent)

K(Cp-2-Pent) (321.1 g, 1.842 mol) and 1 L of pentane were placed under nitrogen in 2 L three necked flask equipped with the stirring bar, thermocouple, and dropping funnel. The flask was connected to the vacuum line under 1 atm of nitrogen. K(Cp-2-Pent) was suspended in pentane (that is, K(Cp-2-Pent) and pentane were forming two liquid layers) by stirring. The deionized and degassed water (100.8 g, 5.526 mol) was placed in the dropping funnel under nitrogen. Water was added under nitrogen to stirred solution of K(Cp-2-Pent) in pentane from the dropping funnel. During the addition of water, temperature in reaction mixture was maintained close to room temperature by any suitable means of cooling (e.g. by external chiller or by adding ice in the secondary container). After all water was added, the resulted mixture was stirred 1 hour under nitrogen, then added more water in air and then the organic layer was separated using the separation funnel. The aqueous solution was washed with pentane and the pentane fractions were combined. The pentane solution was dried with $MgSO_4$ and then $MgSO_4$ was filtered off. The filtrate was placed in 2 L flask and pentane striped under vacuum affording 237.6 g of product. The product was the mixture of $C_5H_5$-2-Pent 85.6% w/w (GC) and pentane 14.4% w/w (GC). Yield of $C_5H_5$-2-Pent 81%. The product was kept below –20° C. to prevent dimerization of $C_5H_5$-2-Pent. $C_5H_5$-2-Pent dimerizes at room temperature with the speed 4.5% per day.

$C_5H_5$-2-Pent and Pentane were separated by fractional distillation, producing a pure (>99%) $C_5H_5$-2-Pent. $^1$H NMR, ($C_6D_6$): 6.51, 6.45, 6.34, 6.22, 6.16, 5.94 (Cp-ring $C_{sp2}$—H of 2 isomers), 2.78, 2.69 (Cp-ring $C_{sp3}$—H of 2 isomers), 2.49 (overlapped multiplet Cp-CHMe(Pr), of two isomers), 1.51, 1.37, 1.28, 1.21 (overlapped multiplets, $CH(CH_2)_2Me$), 1.13, 1.05 (d, 3H, CH-Me of two isomers), 0.98, 0.95 (overlapped triplets $CH_2$-Me, of two isomers). The structures of the two isomers are as follows.

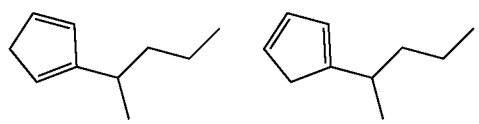

The disclosed method, hydrolysis of potassium compound, produces the pure mono-substituted cyclopentadiene ligand (e.g., $C_5H_5$-2-Pent) in a high yield applying a relatively simple and fast procedure. Potassium salt is a very stable compound and may be shipped to any location or stored for a long time under the nitrogen atmosphere before using it for synthesis, hence this is very convenient starting compound for a simple preparation of pure ligand.

Example 13. Synthesis of In(Cp-2-Pent)

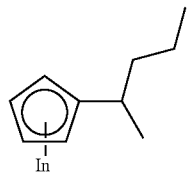

The given example is provided to demonstrate that In(Cp-2-Pent) could be prepared only from lithium compound Li(Cp-2-Pent) and InCl and only in ether, as shown in Table 3.

M(Cp-2-Pent) (3-20 mmol) (M=Li, Na, K) was mixed with the stoichiometric amount of In(Hal) (Hal=Cl, Br, I), solvent added and the mixture stirred for a given time at selected temperature. Then the mixture filtered, solvent removed under vacuum at room temperature, then the residue kept under vacuum in the range from room temperature to 70° C. and all volatiles collected in the separate flask cooled by the liquid nitrogen. The residue after the solvent stripping and vacuum distillation at room temperature to 70° C. weighted and analyzed by FTIR and NMR.

TABLE 3

Reactions to prepare In(Cp-2-Pent).

| Batch # | Reaction | Solvent | Time, Temp. | Observations |
|---|---|---|---|---|
| (1) | 1K(Cp-2-Pent) + 1InCl | Et$_2$O | 1 d at r.t. | No reaction |
| (2) | 1K(Cp-2-Pent) + 1InCl | Et$_2$O | 5 d at r.t. | No reaction |
| (3) | 1Na(Cp-2-Pent) + 1InCl | Mineral oil | 2 h, 120-160° C. | Indium metal formed. Yield of In(Cp-2-Pent) 8%. |
| (4) | 1K(Cp-2-Pent) + 1InCl | neat | 2 h, 60-150° C. | No reaction |
| (5) | 1K(Cp-2-Pent) + 1InCl | Et$_2$O | 6 h, 80-85° C. | No reaction |
| (6) | 1K(Cp-2-Pent) + 1InBr | Et$_2$O | 3 d, r.t. | Incomplete, non-selective reaction. Yield of In(Cp-2-Pent) 22% |
| (7) | 1K(Cp-2-Pent) + 1InI | Et$_2$O | 3 d, r.t. | Incomplete non-selective reaction. Yield of In(Cp-2-Pent) 25% |
| (8) | 1Li(Cp-2-Pent) + 1InCl | Et$_2$O | 4 h, r.t. | Complete and selective reaction. Isolated Yield of In(Cp-2-Pent) 83% |

Sodium and potassium compounds do not react with InCl, while InI and InBr afford the targeted indium complex in a low yield and with unsuitable selectivity, the products contains 2.5-3.0% of InCp and up to 9% of the ligand C$_5$H$_5$-2-Pent. Only lithium compound Li(Cp-2-Pent) and InCl (reaction 8) in ether produce In(Cp-2-Pent) in a high yield and with the high selectivity.

Example 14. Scale-Up Synthesis of In(Cp-2-Pent)

2 L flask with Li(Cp-2-Pent) (129.9 g, 0.91 mol) was charged with InCl (137.3 g, 0.91 mol) and ether (529 g) at room temperature, stirring started and continued overnight, next day visually InCl disappeared and a fine grey suspension was present. This suspension was filtered through the medium size glass frit (in GB), filtrate collected in the second 2 L flask. Ether solvent is stripped until the temperature of liquid inside the second 2 L flask is about 15° C. to room temperature. The obtained crude reaction product containing 90-95% of In(Cp-2-Pent) is subjected to fractional distillation under vacuum. The first fraction collected in a receiver cooled with dry ice/isopropanol at 50-73.1° C. and 3-4 mTorr vacuum contained C$_5$H$_5$-2-Pent and InCp that were discharged. The second fraction collected in to separate receiver cooled with dry ice/isopropanol at 73.1-73.7° C. and 3-4 mTorr vacuum contained In(Cp-2-Pent) with purity more than 98%.

Starting from crude In(Cp-2-Pent) (185.5 g), containing 1.6% Et$_2$O, 2.7% H(Cp-2-Pent), 95.5% In(Cp-2-Pent) and 0.2% In(Cp-2-Pent)$_n$ (n=2,3) according to GC integration, collected in the 1$^{st}$ fraction is 24.7 g (13.3% C$_5$H$_5$-2-Pent and 86.6% In(Cp-2-Pent) (GC integration)), in 2$^{nd}$ fraction 156.4 g (0.9% C$_5$H$_5$-2-Pent and 99.0% In(Cp-2-Pent)) (GC integration)), and remaining in a pot 2.2 g of red liquid, which is a mixture of In(Cp-2-Pent)$_n$ (n=1-3) according to GC. In(Cp-2-Pent) is a brand new compound (CAS No: 2364634-67-1).

Although the subject matter described herein may be described in the context of illustrative implementations to process one or more computing application features/operations for a computing application having user-interactive components the subject matter is not limited to these particular embodiments. Rather, the techniques described herein may be applied to any suitable type of user-interactive component execution management methods, systems, platforms, and/or apparatus.

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

While embodiments of this invention have been shown and described, modifications thereof may be made by one skilled in the art without departing from the spirit or teaching of this invention. The embodiments described herein are exemplary only and not limiting. Many variations and modifications of the composition and method are possible and within the scope of the invention. Accordingly, the scope of protection is not limited to the embodiments described herein, but is only limited by the claims which follow, the scope of which shall include all equivalents of the subject matter of the claims.

What is claimed is:
1. A metal cyclopentadienyl complex having the following formula:

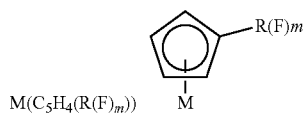

$M(C_5H_4(R(F)_m))$ wherein m≥0; M is an alkali or transition metal; C$_5$H$_4$ represents a cyclopentadienyl (Cp) ring where two hydrogens are substituted by M and R(F)$_m$, respectively; R(F)$_m$ is connected to any one of the carbon atoms of the Cp and selected from
a C$_1$-C$_8$ linear or branched, saturated or unsaturated fluorohydrocarbyl group containing at least one fluorine.
2. The metal cyclopentadienyl complex of claim 1, wherein R is selected from n-Pr, i-Pr, n-Bu, i-Bu, 2-Bu, n-Pent, i-Pent, 2-Pent, n-Hex, i-Hex, 2-Hex, n-Hept, i-Hept, 2-Hept, —CF$_3$, −1,1,1-trifluoropropane (−1,1,1-PrF$_3$), −1,1,1-trifluorobutane (−1,1,1-BuF$_3$), or −1-fluorobutane (−1,1,1-BuF).

3. The metal cyclopentadienyl complex of claim 1, wherein M is selected from K, Na, Sr, Ba, Ga, In, Y or Yb.

4. The metal cyclopentadienyl complex of claim 1 being Li($C_5H_4$-2-$C_5H_{11}$) (Li(Cp-2-Pent), CAS No: 2413046-23-6), K($C_5H_4$-2-$C_5H_{11}$) (K(Cp-2-Pent)), Na($C_5H_4$-2-$C_5H_{11}$) (Na(Cp-2-Pent)), K($C_5H_4$-1-F—$C_4H_{10}$) (K(Cp-1-F-Bu)), K($C_5H_4$-1,1,1-3F—$C_4H_6$) (K(Cp-1,1,1-3F-Bu)), Li($C_5H_4$-2-$C_4H_9$) (Li(Cp-2-Bu)), or In($C_5H_4$-2-$C_5H_{11}$) (In(Cp-2-Pent), CAS No.: 2364634-67-1).

5. The metal cyclopentadienyl complex of claim 1 being In($C_5H_4$-2-$C_5H_{11}$) (In(Cp-2-Pent), CAS No.: 2364634-67-1).

6. The metal cyclopentadienyl complex of claim 1 being Li($C_5H_4$-2-$C_5H_{11}$) (Li(Cp-2-Pent), CAS No: 2413046-23-6).

* * * * *